US011222425B2

(12) United States Patent
Tang et al.

(10) Patent No.: US 11,222,425 B2
(45) Date of Patent: Jan. 11, 2022

(54) ORGANS AT RISK AUTO-CONTOURING SYSTEM AND METHODS

(71) Applicant: DeepVoxel, Inc., Irvine, CA (US)

(72) Inventors: Hao Tang, Irvine, CA (US); Yang Liu, Foster City, CA (US); Shanlin Sun, Irvine, CA (US); Narisu Bai, Riverside, CA (US)

( * ) Notice: Subject to any disclaimer, the term of this patent is extended or adjusted under 35 U.S.C. 154(b) by 87 days.

(21) Appl. No.: 16/787,396

(22) Filed: Feb. 11, 2020

(65) Prior Publication Data

US 2021/0248747 A1 Aug. 12, 2021

(51) Int. Cl.
| | | |
|---|---|---|
| *G06K 9/00* | (2006.01) | |
| *G06T 7/11* | (2017.01) | |
| *G06T 7/00* | (2017.01) | |
| *G06K 9/46* | (2006.01) | |
| *G16H 30/40* | (2018.01) | |
| *G06N 3/08* | (2006.01) | |
| *A61N 5/10* | (2006.01) | |
| *G16H 20/40* | (2018.01) | |

(52) U.S. Cl.
CPC .............. *G06T 7/11* (2017.01); *A61N 5/1039* (2013.01); *G06K 9/46* (2013.01); *G06N 3/08* (2013.01); *G06T 7/0012* (2013.01); *G16H 20/40* (2018.01); *G16H 30/40* (2018.01); *G06K 2209/051* (2013.01); *G06T 2207/10072* (2013.01); *G06T 2207/20084* (2013.01); *G06T 2207/20132* (2013.01); *G06T 2207/30061* (2013.01)

(58) Field of Classification Search
CPC .................................................... G06T 7/0012
See application file for complete search history.

(56) References Cited

U.S. PATENT DOCUMENTS

| | | | |
|---|---|---|---|
| 9,589,374 B1* | 3/2017 | Gao | G06T 11/008 |
| 2016/0140725 A1* | 5/2016 | Bergner | G06T 7/136 |
| | | | 382/173 |
| 2017/0199261 A1* | 7/2017 | Farr | G01R 33/56509 |
| 2019/0030371 A1* | 1/2019 | Han | G16H 50/20 |
| 2019/0192880 A1* | 6/2019 | Hibbard | A61N 5/1039 |
| 2020/0155868 A1* | 5/2020 | Yuan | G06N 3/08 |
| 2021/0035305 A1* | 2/2021 | Fang | G06N 3/0454 |

\* cited by examiner

*Primary Examiner* — Hadi Akhavannik
(74) *Attorney, Agent, or Firm* — Cionca IP Law P.C.; Marin Cionca

(57) ABSTRACT

A system and methods for automatically delineating OARs in whole-volume medical images through a two-stage DCNN model, the DCNN model comprising an OAR detection network and an OAR segmentation network, and the method comprising the steps of: inputting the whole-volume medical images to the OAR detection network; extracting image features through a sequence of downsampling blocks; generating a final detection feature map via upsampling and concatenation; detecting at least one OAR candidate by branching the final detection feature map, wherein the at least one OAR candidate is defined by a predicted bounding box with a class label; inputting the predicted bounding box and corresponding class label to the OAR segmentation network; cropping the final detection feature map and a downsampling block in the OAR detection network according to the predicted bounding box; concatenating the cropped feature maps and generating a predicted binary mask delineating OARs according to the class label.

16 Claims, 18 Drawing Sheets

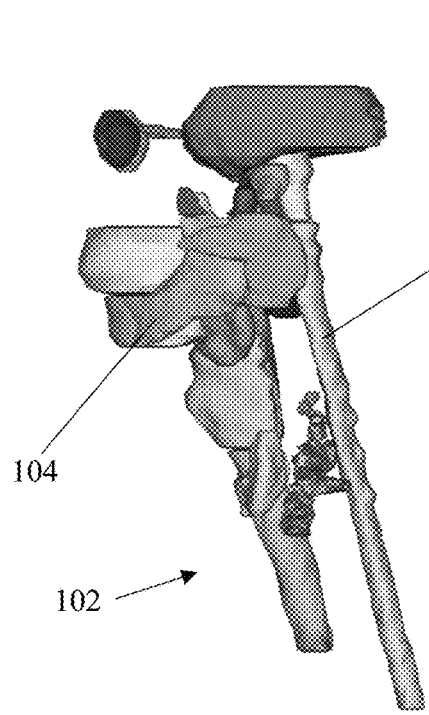
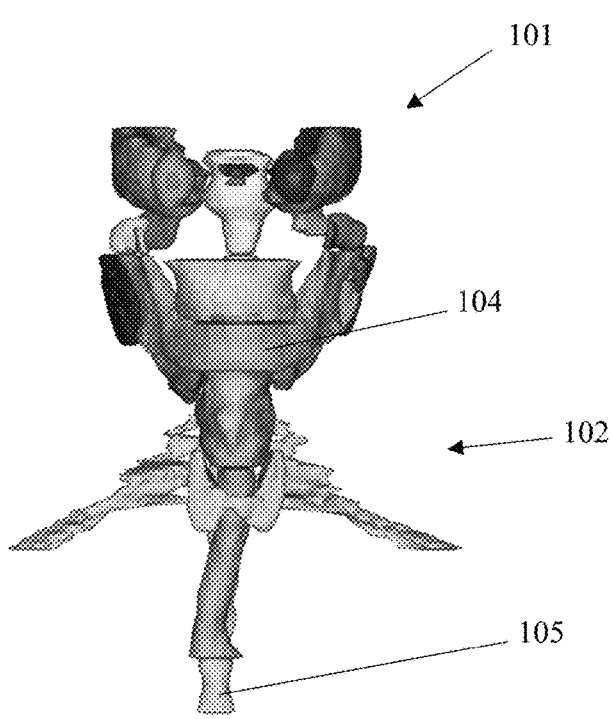
FIG. 1A
FIG. 1B
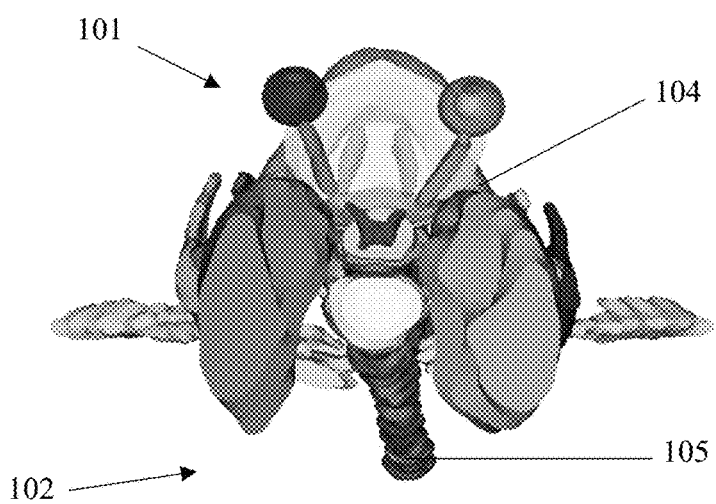
FIG. 1C

| DSC comparison on the test set of dataset 1 | | | | | |
|---|---|---|---|---|---|
| OAR | MAS | AnatomyNet | $U_a$-Net | Human | Human* |
| Brachial plexus | 30.38 ± 15.63 | 50.41 ± 8.08 | 56.15 ± 10.83 | 33.03 ± 7.83 | 33.03 ± 7.83 |
| Brain stem | 82.25 ± 7.47 | 82.63 ± 4.57 | 86.25 ± 3.86 | 80.25 ± 4.63 | 83.47 ± 4.35 |
| Constrictor naris | 66.38 ± 8.21 | 73.68 ± 7.56 | 76.46 ± 6.13 | 62.34 ± 8.63 | 62.34 ± 8.63 |
| Ear L | 70.38 ± 14.94 | 76.68 ± 9.00 | 77.28 ± 4.25 | 43.57 ± 12.63 | 43.57 ± 12.63 |
| Ear R | 70.03 ± 15.57 | 78.77 ± 5.77 | 78.64 ± 6.35 | 39.71 ± 10.81 | 39.71 ± 10.81 |
| Eye L | 85.96 ± 10.99 | 88.41 ± 3.10 | 92.51 ± 2.00 | 90.71 ± 2.11 | 90.71 ± 2.11 |
| Eye R | 82.68 ± 17.38 | 89.25 ± 3.38 | 92.49 ± 2.34 | 91.51 ± 1.79 | 91.51 ± 1.79 |
| Hypophysis | 43.54 ± 18.45 | 56.18 ± 10.03 | 63.86 ± 8.73 | 59.26 ± 14.77 | 60.15 ± 15.07 |
| Larynx | 82.60 ± 8.19 | 83.08 ± 7.98 | 89.25 ± 3.26 | 68.60 ± 6.59 | 68.60 ± 6.59 |
| Lens L | 46.25 ± 24.79 | 77.25 ± 7.92 | 81.90 ± 6.88 | 64.27 ± 10.06 | 64.27 ± 10.06 |
| Lens R | 45.53 ± 23.94 | 78.06 ± 7.51 | 83.04 ± 5.90 | 71.79 ± 9.59 | 71.79 ± 9.59 |
| Mandible | 83.95 ± 11.48 | 91.97 ± 1.71 | 93.12 ± 1.41 | 90.97 ± 1.46 | 90.97 ± 1.46 |
| Optic chiasm | 42.08 ± 17.52 | 60.55 ± 11.36 | 64.21 ± 16.39 | 28.61 ± 14.40 | 69.66 ± 13.26 |
| Optic nerve L | 59.49 ± 14.61 | 72.55 ± 6.55 | 75.73 ± 7.26 | 65.10 ± 8.44 | 69.80 ± 8.67 |
| Optic nerve R | 59.08 ± 16.53 | 72.96 ± 7.90 | 76.06 ± 6.49 | 66.14 ± 7.29 | 68.70 ± 8.85 |
| Oral cavity | 86.10 ± 9.11 | 87.69 ± 5.67 | 90.77 ± 2.32 | 79.30 ± 3.59 | 79.30 ± 3.59 |
| Parotid L | 72.52 ± 15.57 | 82.28 ± 6.71 | 84.86 ± 4.22 | 78.46 ± 4.90 | 78.46 ± 4.90 |
| Parotid R | 71.20 ± 17.55 | 82.20 ± 7.26 | 84.93 ± 3.99 | 78.88 ± 4.41 | 78.88 ± 4.41 |
| SMG L | 60.89 ± 12.11 | 75.47 ± 8.93 | 80.71 ± 7.32 | 72.73 ± 6.25 | 72.73 ± 6.25 |
| SMG R | 63.70 ± 15.80 | 74.82 ± 14.69 | 82.54 ± 7.47 | 74.10 ± 16.92 | 74.10 ± 16.92 |
| Spinal cord | 77.42 ± 16.70 | 80.32 ± 6.48 | 85.84 ± 5.90 | 84.59 ± 6.62 | 84.59 ± 6.62 |
| Sublingual gland | 21.52 ± 16.34 | 39.94 ± 21.02 | 45.99 ± 18.84 | 35.16 ± 23.87 | 35.16 ± 23.87 |
| Temporal lobe L | 80.05 ± 7.28 | 81.76 ± 5.33 | 84.78 ± 2.62 | 82.41 ± 5.01 | 82.79 ± 4.53 |
| Temporal lobe R | 78.26 ± 7.40 | 72.97 ± 14.60 | 84.13 ± 3.34 | 80.90 ± 7.49 | 81.40 ± 7.62 |
| Thyroid | 63.68 ± 19.65 | 71.82 ± 11.40 | 85.62 ± 4.63 | 82.42 ± 6.16 | 82.42 ± 6.16 |
| TMJ L | 61.26 ± 19.86 | 86.65 ± 3.34 | 87.96 ± 3.12 | 84.67 ± 5.09 | 84.67 ± 5.09 |
| TMJ R | 63.45 ± 20.48 | 85.73 ± 3.69 | 86.86 ± 3.60 | 81.98 ± 8.59 | 81.98 ± 8.59 |
| Trachea | 65.86 ± 18.75 | 79.34 ± 7.75 | 81.29 ± 4.84 | 91.05 ± 1.69 | 91.05 ± 1.69 |
| Average | 64.87 | 76.19 | 80.43 | 70.38 | 72.17 |

Values are given in units of %. L, left; R, right; SMG, submandibular gland; TMJ, temporomandibular joint; MAS, multi-atlas segmentation. Bold numbers represent the best results. *The same radiation oncologist modified his/her previous delineation by referencing the corresponding MRI images.

FIG. 13

| Average 95th percentile HD comparison on the test set of Dataset 1 | | | | | |
|---|---|---|---|---|---|
| OAR | MAS | AnatomyNet | $U_\alpha$-Net 1408 | Human | Human² |
| Brachial plexus | 30.73±25.99 | 37.97±36.44 | 18.27±14.53 | 43.20±18.19 | 43.20±18.19 |
| Brain stem | 6.62±2.99 | 5.30±1.36 | 4.75±1.58 | 5.04±1.28 | 4.89±1.22 |
| Constrictor naris | 9.49±8.78 | 8.14±6.20 | 5.71±3.34 | 12.92±7.57 | 12.92±7.57 |
| Ear L | 9.81±19.85 | 25.88±76.28 | 5.04±1.35 | 11.08±3.49 | 11.08±3.49 |
| Ear R | 9.01±16.04 | 23.28±68.48 | 4.67±1.42 | 13.44±3.31 | 13.44±3.31 |
| Eye L | 4.73±4.53 | 2.97±0.54 | 2.44±0.75 | 3.03±0.67 | 3.03±0.67 |
| Eye R | 6.37±7.95 | 2.95±0.54 | 2.52±1.16 | 3.62±0.61 | 3.62±0.61 |
| Hypophysis | 5.25±2.33 | 3.62±0.74 | 3.23±0.79 | 3.25±0.80 | 3.20±0.96 |
| Larynx | 11.53±11.14 | 64.29±89.53 | 6.15±5.83 | 13.35±7.26 | 13.35±7.26 |
| Lens L | 5.69±7.02 | 2.32±0.82 | 1.95±0.80 | 2.98±0.63 | 2.98±0.63 |
| Lens R | 6.77±9.82 | 2.00±0.74 | 2.07±1.35 | 2.50±0.76 | 2.50±0.76 |
| Mandible | 8.19±12.53 | 7.14±21.95 | 2.48±0.83 | 2.54±0.30 | 2.54±0.30 |
| Optic chiasm | 7.34±3.89 | 4.45±1.19 | 4.58±2.36 | 6.90±1.81 | 4.19±1.70 |
| Optic nerve L | 6.94±4.54 | 5.28±3.68 | 3.31±0.93 | 4.35±1.29 | 3.75±1.12 |
| Optic nerve R | 7.53±7.52 | 4.67±1.84 | 3.11±1.31 | 4.09±1.24 | 3.61±1.05 |
| Oral cavity | 12.65±9.60 | 12.79±21.54 | 7.38±2.05 | 11.83±3.10 | 11.83±3.10 |
| Parotid L | 11.49±15.45 | 19.29±65.05 | 6.98±3.83 | 8.83±3.65 | 8.83±3.65 |
| Parotid R | 11.22±12.84 | 20.67±63.34 | 6.28±2.87 | 8.54±4.22 | 8.54±4.22 |
| SMG L | 8.87±3.47 | 6.49±4.00 | 6.75±4.65 | 6.86±3.72 | 6.86±3.72 |
| SMG R | 12.14±14.42 | 6.59±4.40 | 5.65±3.99 | 6.40±3.12 | 6.40±3.12 |
| Spinal cord 1472 | 6.09±5.54 | 99.72±80.01 | 6.86±22.03 | 9.04±18.95 | 9.04±18.95 |
| Sublingual gland | 13.00±12.93 | 7.56±3.29 | 7.46±3.07 | 9.19±3.88 | 9.19±3.88 |
| Temporal lobe L | 13.19±4.85 | 12.03±4.34 | 11.32±3.73 | 8.32±2.71 | 9.79±4.69 |
| Temporal lobe R | 14.73±5.27 | 16.17±6.21 | 13.58±4.52 | 9.64±4.06 | 10.22±5.57 |
| Thyroid | 12.52±13.93 | 128.99±83.86 | 3.94±2.43 | 5.93±6.44 | 5.93±6.44 |
| TMJ L | 7.74±6.78 | 12.21±25.05 | 2.79±1.09 | 2.96±1.30 | 2.96±1.30 |
| TMJ R | 10.29±18.13 | 28.13±79.13 | 2.74±0.68 | 2.88±0.98 | 2.88±0.98 |
| Trachea | 33.68±18.21 | 43.91±56.11 | 20.86±8.99 | 2.57±1.26 | 2.57±1.26 |
| Average | 10.84 | 21.98 | 6.21 | 8.01 | 7.94 |

Values are given in units of mm. L, left; R, right; SMG, submandibular gland; TMJ, temporomandibular joint. Bold numbers represent the best results. ²The same radiation oncologist modified his/her previous delineation by referring to the corresponding MRI images.

FIG. 14

| | Time comparison for an oncologist delineating using two approaches | | | | |
|---|---|---|---|---|---|
| | Tumour category | Mode 1 (min) | Mode 2 (min) | t | P |
| PA1 | NPC | 35 | 13 | | |
| PA2 | NPC | 33 | 11 | | |
| PA3 | NPC | 30 | 13 | | |
| PA4 | NPC | 38 | 20 | | |
| PA5 | HD | 36 | 11 | | |
| PA6 | BM | 34 | 12 | | |
| PA7 | NPC | 32 | 8 | | |
| PA8 | NPC | 33 | 14 | | |
| PA9 | BM | 35 | 15 | | |
| PA10 | BM | 30 | 14 | | |
| Average | | 33.60 ± 2.55 | 13.10 ± 3.14 | 21.68 | $4.5 \times 10^{-9}$ |

NPC, nasopharyngeal carcinoma; HD, Hodgkin disease; MD, brain metastasis. Mode 1 refers to delineation performed completely manually, without any assistance of computational tools, and mode 2 refers to delineation done by modifying the delineation result generated by the proposed method. t denotes the paired t-test statistic and P denotes the P value.

FIG. 15

ORGANS AT RISK AUTO-CONTOURING SYSTEM AND METHODS

BACKGROUND OF INVENTION

1. Field of the Invention

The invention relates generally to radiation therapy and more specifically to using deep convolution neural network models to automatically delineate organs at risk for radiation therapy.

2. Description of the Related Art

A key step in radiation therapy (RT), which is one of the most widely used therapies for the treatment of cancers, is delineating organs at risk (OARs). OARs, which are normal and/or healthy organs, may be adversely affected if exposed to radiation during RT, particularly organs that lie in the head and neck, thorax, and abdomen regions. Damaging normal organs in these regions of the body can result in a series of complications, such as xerostomia, oral mucosal damage, dysphagia, visual deterioration, hearing loss and cognitive impairment. Delineating OARs therefore helps mitigate the side effects of irradiation during RT by protecting these organs during radiotherapy.

Currently, delineation of OARs is done manually by human experts who examine 3D computed tomography (CT) images and/or scans. This manual process of examining CT scans to delineate OARs is time-consuming and error-prone due to the anatomical complexity of certain organs in the human body.

Furthermore, current deep learning-based OAR delineation methods (e.g., U-Net, AnatomyNet) are unreliable since the networks are not capable of processing whole-volume medical images (i.e., 3D CT scans), and can only segment OARs on a slice-by-slice basis (i.e., 2D slices of a 3D scan). Segmenting OARs one slice of the 3D image at a time prevents a system from constraining rough locations and sizes of OARs, which can produce false positives (i.e., incorrect predictions). Additionally, these methods are computationally intensive, taking minutes or hours to complete, and because of their reliance on image templates, the methods cannot adequately account for anatomical variations (e.g., variations due to the growth of tumors).

Therefore, there is a need to solve the problems described above by providing a reliable, lightweight and well-tested deep convolutional neural network (DCNN) model and methods for automatically delineating OARs in 3D medical images of the body.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, an end-to-end two-stage deep learning OAR delineation framework is provided having an OAR Detection Network and an OAR Segmentation Network and is adapted to run on easily accessible commodity graphics processing units. The OAR Detection Network, operating during the first stage, and the OAR Segmentation Network, operating during the second stage, function in a successive manner. Both networks share the same feature extractor model based on three-dimensional (3D) convolution. The OAR delineation framework is trainable and can learn to extract a hierarchy of complex image features from input data and utilize the features to segment anatomical structures without mapping an image to templates. Therefore, the OAR delineation framework does not need to store image templates in graphics processing unit (GPU) memory. Thus, an advantage may be that the OAR delineation framework may be implemented as a lightweight model with low GPU memory cost. Another advantage may be the significant reduction in the amount of time spent by a clinician to manually delineate OARs. Another advantage may be that the OAR delineation framework is capable of segmenting OARs in the head and neck, thorax, and abdomen regions from whole-volume CT images, allowing for better capture of the shapes, sizes and locations of organs. An additional advantage of the end-to-end two-stage OAR delineation framework may be the optimization of both stages jointly, allowing for a time-efficient and well-trained delineation solution.

In another aspect, an OAR Detection Network is provided with downsample and upsample blocks that extract a hierarchy of complex image features from input data. The OAR Detection Network takes a CT scan as input and identifies the approximate size and location of each OAR in the CT scan, in the form of a predicted bounding box, as well as a classification for each OAR. The OAR Detection Network also suppresses false-positive predictions outside the normal range of each OAR known to the framework. Thus, an advantage of the OAR Detection Network may be that it forces the OAR Segmentation Network to only focus on local image patches rather than the whole volume, substantially reducing the GPU memory cost. An additional advantage of the OAR Detection Network may be that the suppression of false positives significantly reduces the amount of time needed to manually remove false positives from a resulting delineation map.

In another aspect, an OAR Segmentation Network is provided with upsample blocks that utilize extracted image features to segment anatomical structures in the form of a contour map. The OAR Segmentation Network takes the outputs of the OAR Detection Network as inputs and utilizes these inputs as a guide, only segmenting OARs from the predicted bounded regions of the first stage. The OAR Detection Network derives a fine-scale segmentation of each OAR and outputs predicted masks of all OARs in an image at once. The OAR Segmentation Network may be provided with a local contrast normalization step that standardizes each 3D response map to zero mean and unit variance across all voxels. This technique allows the OAR Segmentation Network to adapt to differing contrasts when segmenting different organs. Thus, an advantage of the OAR Segmentation Network may be that the 3D OAR prediction contour map is outputted on the original 3D CT input image in the original image resolution. An additional advantage of the OAR Segmentation Network may be the significant reduction in time spent by a clinician manually delineating OARs in a 3D CT image, if needed.

In another aspect, a training method is provided to train the two-stage deep learning framework using training data comprising a dataset of CT scans and manually delineated OARs. The training data, as an example, comprises a dataset of 215 CT scans and 28 (twenty-eight) manually delineated OARs. The training method runs the two-stage deep learning framework over the training data so that the framework can learn to extract a hierarchy of complex image features according to the dataset of CT scans. The training method may be provided with a detection loss function and classification loss function that minimize the error in detecting OAR candidates. The training method also trains the framework to learn to segment anatomical structures according to the manually delineated OARs, which may be done via a segmentation loss function. The training method and training data provided enable the OAR delineation framework to be implemented without high GPU memory (e.g., 11 GB memory), since only a portion of the image features need to be upsampled. Thus, an advantage of the training method and data may be that the deep learning OAR delineation framework can accurately and automatically delineate OARs in a CT image. Another advantage of the training method and data may be the reduction in memory cost and overall hardware weight of the OAR delineation framework.

In another aspect, a region separation method is provided to automatically separate the head and neck, thorax, and abdomen regions in whole-volume medical images of the body for delineation of OARs in these regions. The region separation method may be utilized prior to the OAR delineation framework and may be provided with a region detection model having a segmentation algorithm, a separation algorithm and a classification algorithm. The region detection model may separate the whole-volume medical images into three parts identifying the head and neck, thorax, and abdomen regions, respectively. The OAR delineation framework may then be applied to each region separately to delineate OARs in each of these regions. Thus, an advantage of the region detection method may be that the user (e.g., radiation oncologist or clinician) does not need to manually separate and classify each region in a whole-volume medical image prior to OAR delineation. Another advantage of the region detection method may be that the method may still accommodate whole-volume medical images containing only a single region of the body, allowing for full implementation of the method in clinical settings.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which:

FIGS. 1A-1C illustrate side, front and top views, respectively, of exemplary OARs to be delineated in the head and neck regions, according to an aspect.

FIG. 13 is a table summarizing an exemplary Dice similarity coefficient comparison of the two-stage deep learning OAR delineation framework with current delineation methods, according to an aspect.

FIG. 14 is a table summarizing an exemplary Hausdorff distance comparison of the two-stage deep learning OAR delineation framework with current delineation methods, according to an aspect.

FIG. 15 is a table summarizing an exemplary time comparison for an oncologist delineating OARs with and without assistance from the two-stage OAR delineation framework, according to an aspect.

DETAILED DESCRIPTION

Figure 2:
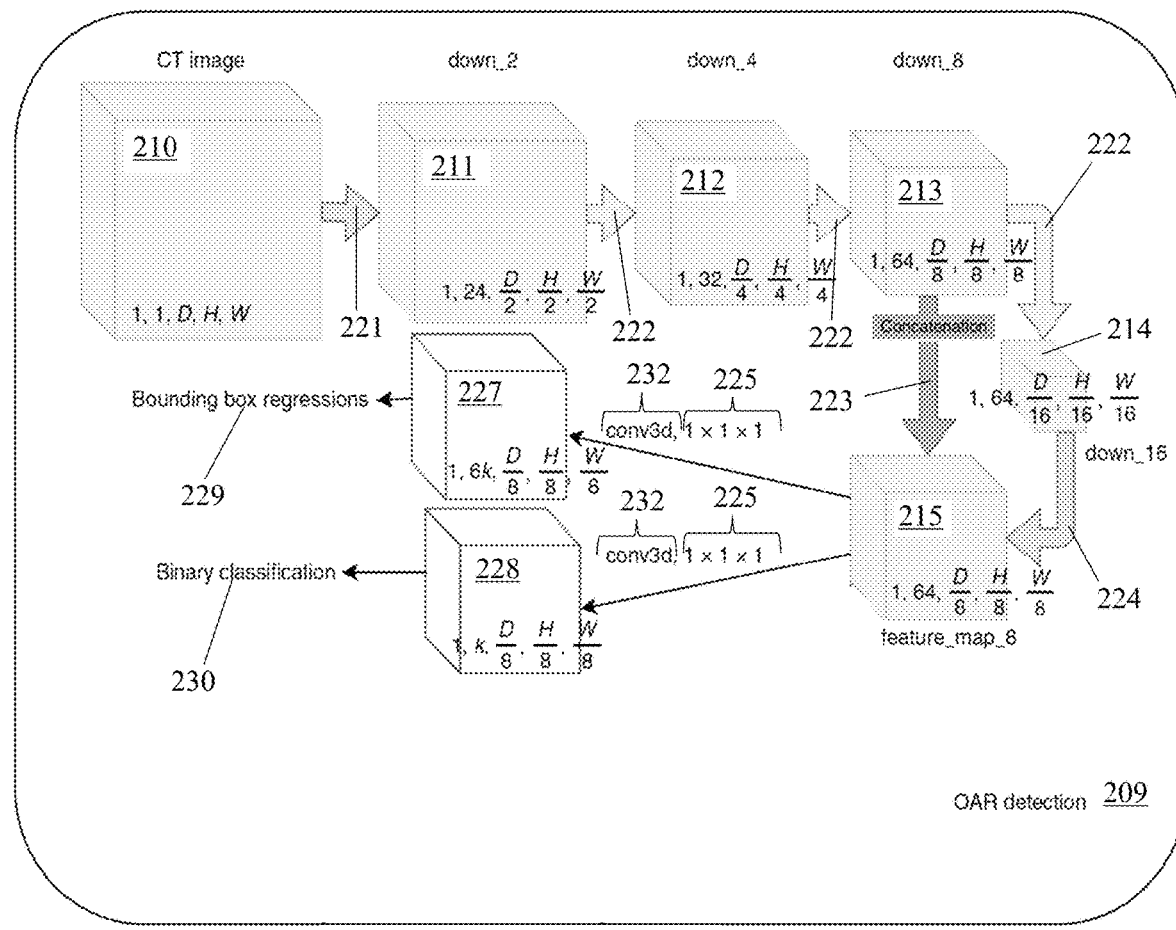
FIG. 2 is a flowchart illustrating an OAR Detection Network of a two-stage deep learning OAR delineation framework, according to several aspects.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

For the following description, it can be assumed that most correspondingly labeled elements across the figures (e.g., 215 and 315, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

FIGS. 1A-1C illustrate side, front and top views, respectively, of exemplary OARs 104, 105 to be delineated in the head 101 and neck 102 regions, according to an aspect. FIGS. 1A-1C depict all the possible OARs that can be found in the head 101 and neck 102 regions of the body, as an example. A two-stage deep learning OAR delineation framework ("two-stage deep learning OAR delineation framework," "deep learning OAR delineation framework," "OAR delineation framework," "OAR framework," "DCNN OAR framework") disclosed herein below is designed and trained to delineate OARs in the human body. As shown in FIGS. 1A-1C as an example, there are a total of 28 (twenty-eight) OARs in the head and neck regions to be delineated for radiation therapy planning, a process which can be time-consuming and quite difficult due to the varying levels of anatomical complexity of each OAR.

As will be discussed in detail herein below, the two-stage deep learning OAR delineation framework may comprise two networks, a first network in the first stage and a second network in the second stage. The first network may be an OAR Detection Network, which will be discussed when referring to FIG. 2, and the second network may be an OAR Segmentation Network, which will be discussed when referring to FIG. 8. As an example, a 3D CT image may be passed into the OAR delineation framework as input containing a scan of the head 101 and neck 102 regions. The OAR delineation framework may process and analyze the 3D CT image to delineate all possible OARs of the 28 OARs shown in FIGS. 1A-1C. Upon completion of the delineation process, the OAR framework may output a contour map (see e.g., FIG. 12C) transposed over the original CT scan identifying all detected OARs (e.g., the mandible 104 and spinal cord 105).

The DCNN disclosed herein may be implemented in a computer system and run on a commodity GPU in a hospital setting, as an example. The computer system may also include an external CT scanner, a PC and a treatment planning system. The PC may receive whole-volume medical images from the CT scanner, wherein the PC runs the disclosed DCNN framework over the whole-volume medical images. The results (delineated OARs) of the DCNN framework are then sent to the treatment planning system for review and any necessary modification by doctors, per the example. In another example, the DCNN OAR delineation framework may be implemented in a cloud service. Whole-volume medical images may be inputted to the DCNN framework running on a website via an online cloud service, wherein the results can be downloaded by a user after processing of the images by the DCNN, per the example.

FIG. 2 is a flowchart illustrating an OAR Detection Network 209 of a two-stage deep learning OAR delineation framework, according to several aspects. As mentioned previously above, the two-stage deep learning OAR delineation framework may comprise the OAR Detection Network ("OAR Detection Network," "Detection Network," "Detection module") 209 as part of the first stage of operation. As shown in FIG. 2, the OAR Detection Network 209 may comprise a series of downsample blocks 211-214 and an upsample block 215. A number of computational operations are performed within the OAR Detection Network 209 that result in the final outputs 229, 230 of the network 209, as will be discussed in detail below.

As shown in FIG. 2, a CT image 210 may be passed into the OAR Detection Network 209 as input to locate a rough estimate of the location and size of each OAR in the CT image 210. As shown, the OAR Detection Network 209 may receive the CT image 210 with dimensions "D, H, W" denoting depth, height and width, respectively. Each block (e.g., 210, 211) may represent a feature map described in terms of its batch size, channel, depth, height, and width, respectively. As shown in FIG. 2 as an example, the CT image 210 possesses a batch size of 1 (one) and a channel equal to 1 (one). The channel parameter denotes the number of patches/layers stacked over one another that make up the given volume (D, H, W) of each input. As shown, the channel size may change at each point along the disclosed process.

As shown, the CT image 210 may pass through a series of downsample blocks 211-214, as an example. The CT image 210 may undergo 3D convolution and resolution reduction at each downsample block in the sequence, which will be discussed in further detail when referring to FIG. 4. A first downsampling stage 221 results in a first downsample block "down_2" 211 comprising the feature map $$\left(1, 24, \frac{D}{2}, \frac{H}{2}, \frac{W}{2}\right),$$

as an example. The down_2 feature map 211 may undergo a sequence of additional downsample blocks 212-214, reducing the resolution by one-half along each axis after each subsequent downsampling 222 (discussed in FIG. 5), as shown as an example. The last downsampling block "down_16" 214 may be upsampled to a final feature map 215 of 64 channels with size $$\left(\frac{D}{8}, \frac{H}{8}, \frac{W}{8}\right)$$

through transposed convolution 224 and by concatenating 223 the feature map 215 with the corresponding downsampling block 213 of the same size, as shown in FIG. 2 as an example.

The final feature map "feature_map_8" 215 may generate and screen OAR candidates defined by bounding box regression 229 and binary classification 230, as shown in FIG. 2. To generate OAR candidates, the final feature map 215 may be branched into two separate heads 227 and 228, as shown. As shown, each branch may undergo 3×3×3 convolution 232 followed by 1×1×1 convolution 225. The first head 227 may generate bounding box regressions 229 and may comprise the feature map $$\left(1, 6k, \frac{D}{8}, \frac{H}{8}, \frac{W}{8}\right),$$

where "k" refers to the number of anchors. The second head 228 may generate binary classification 230 and may comprise the feature map $$\left(1, k, \frac{D}{8}, \frac{H}{8}, \frac{W}{8}\right),$$

as shown as an example. Each bounding box may be represented by a rectangular cuboid defined by six parameters t=(x, y, z, d, h, w), with (x, y, z) denoting the bounding box center (i.e., location) and (d, h, w) denoting the depth, height, and width (i.e., size) in the original CT image coordinates.

As mentioned above, the k parameter in each feature map denotes the anchor, and 12 (twelve) anchors are used to generate the OAR candidates at each sliding window. The anchors k may produce a list of bounding boxes 229 for each OAR candidate. As an example, let there be k anchors at each voxel in each feature map, where each voxel in the feature map can be mapped to a point in the original image coordinates. Each anchor k represents a predefined bounding box size, for example a bounding box of (30, 30, 30) denoting (depth, height, width) voxels. Such an anchor serves as the OAR delineation framework's initial guess that an OAR may exist inside the region defined by the anchor's location and size. The OAR Detection Network then classifies these initial guesses (i.e., anchors) as to whether or not they contain an OAR, as an example. Bounding boxes 229 define each of these OAR candidates, which is of a particular size and at a particular location, and the binary classification 230 defines an OAR designation for each OAR candidate.

Figure 3:
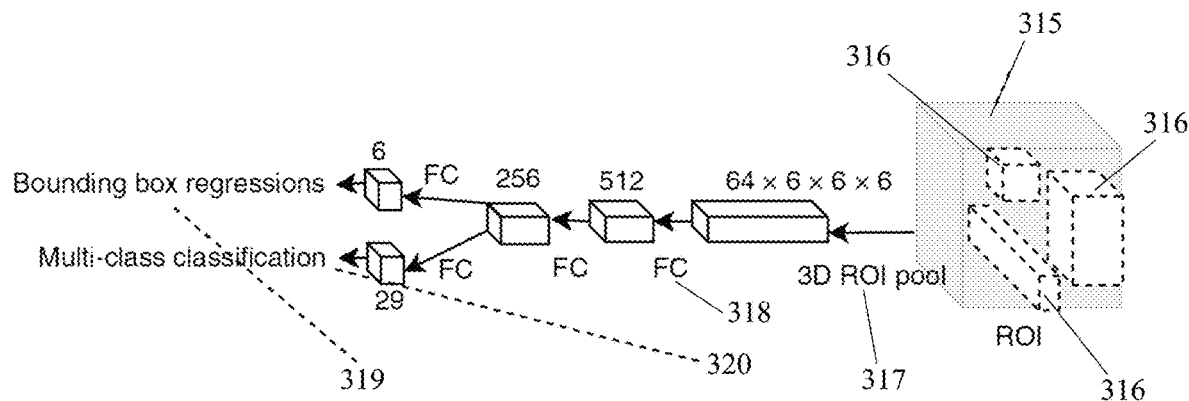
FIG. 3 is a flowchart illustrating the feature_map_8 element 215 shown in FIG. 2, according to an aspect.

FIG. 3 is a flowchart illustrating the feature_map_8 element 215 shown in FIG. 2, according to an aspect. As discussed previously above, detected OAR candidates 316 may be defined according to bounding box regressions (229 in FIG. 2) and binary classification (230 in FIG. 2). As shown in FIG. 3, the detected OAR candidate bounding boxes 316 in the feature_map_8 315 Region of Interest (ROI) may further undergo a 3D ROI-pooling step 317 to generate feature maps of fixed sizes and classify the OAR candidates. As shown in FIG. 3, the ROI-pooling step 317 is applied to image features extracted from the feature_map_8 315 ROI in regions specified by each predicted bounding box 316. The ROI-pooling step 317 produces a feature map with fixed dimensions by reducing the spatial size of the representation, denoted by "64×6×6×6" as shown. As an example, two fully connected (FC) layers 318 may be subsequently applied to classify each OAR prediction into one of 29 classes (28 possible OARs plus one background) and to further regress coordinates and size offsets of each bounding box 316. The FC layers allow full connections to all activations in the previous layer, as an example. As shown, the result of this classification step is the bounding box regression 319 with the corresponding multi-class classification 320.

The final output of the OAR Detection Network (209 in FIG. 2) is the predicted bounding box (x̂, ŷ, ẑ, d̂, ĥ, ŵ) in the original image coordinates, with the corresponding class label ĉ for each OAR, as will be described further when referring to FIG. 8.

Figure 4:
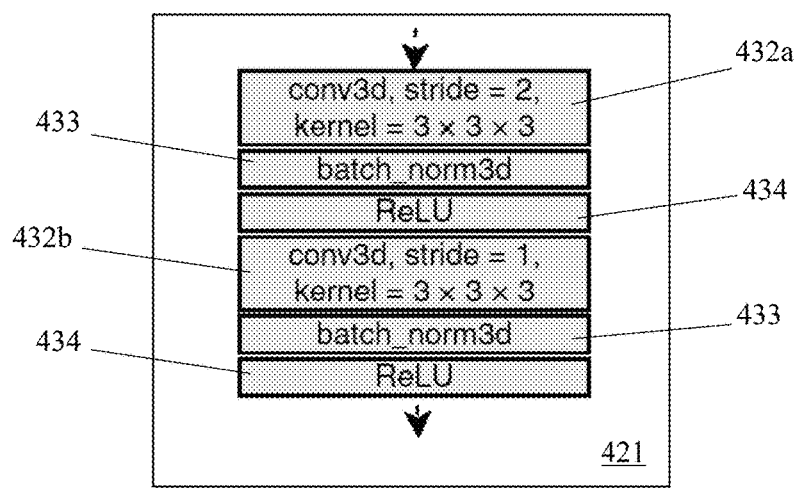
FIG. 4 is a flowchart illustrating the first downsampling element 221 shown in FIG. 2, according to an aspect.

FIG. 4 is a flowchart illustrating the first downsampling element 221 shown in FIG. 2, according to an aspect. As shown in FIG. 4 and throughout this disclosure, several modules taken from the open source machine learning framework PyTorch® were used to develop the delineation method. As similarly described when referring to FIG. 2, the downsampling stage 421 may perform 3D convolution on an input CT image and reduce the resolution of the CT image. As shown in FIG. 4, the input image may enter a first 3D convolution module 432a, which may be represented by the function "conv3d." The 3D convolution module 432a performs a spatial convolution over the input signal composed of volumes. The "stride" parameter specifies the strides of the convolution along each spatial dimension. The "kernel" parameter specifies the depth, width and height of the 3D convolution window. As shown as an example, the kernel is set to 3×3×3 to specify the volume of the convolution window. The stride parameter is set to 2 (two), in this example, to specify two strides of convolution. This layer creates a convolution kernel that is convolved with the layer input to produce a tensor of outputs. The output tensor of the 3D convolution module 432a may enter a batch normalization module 433, which can be represented by the function "batch_norm3d." Within the batch_norm3d module 433, the dimensions of the previous layer are normalized at each batch, such that the mean deviation is maintained close to 0 (zero) and the standard deviation is maintained close to 1 (one).

The output of the batch normalization module 433 may then pass into an activation function module 434, as shown in FIG. 4. The activation function module 434 may be represented by the rectified linear activation unit "ReLU," which applies a piecewise linear function on the input. The ReLU function 434 will output the input value directly if the value is positive, otherwise, the function 434 will output 0 (zero). The output of the ReLU module 434 may be passed into a second 3D convolution module 432b, which may again utilize the function "conv3d." As shown, the stride parameter is set to "1" in this example to specify one stride of convolution along each spatial dimension. As shown, the kernel parameter is again set to 3×3×3 to specify the three-dimensional volume of the convolution window. The output tensor of the 3D convolution module 432b may enter a second batch normalization module 433, which can be represented by the function "batch_norm3d." Again, the dimensions of the previous layer are normalized at each batch, as an example. The output of the batch normalization module 433 may pass through a final activation function ReLU 434, wherein a piecewise linear function is applied on the signal to transform the summed weighted input into the activation output for that input. As discussed previously when referring to FIG. 2, the output of the ReLU activation function 434 is the downsample block "down_2" (shown by 211), which may consist of the feature map $$\left(1, 24, \frac{D}{2}, \frac{H}{2}, \frac{W}{2}\right),$$

as an example.

Figure 5:
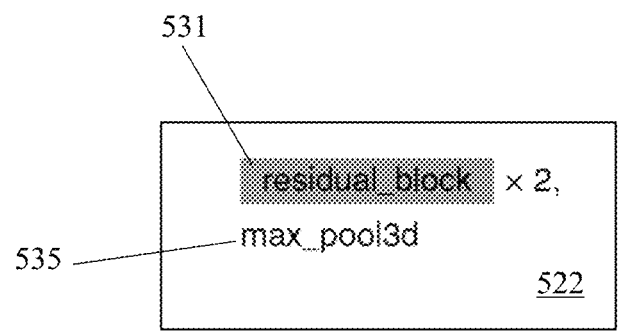
FIG. 5 is a flowchart illustrating the second downsampling element 222 shown in FIG. 2, according to an aspect.

FIG. 5 is a flowchart illustrating the second downsampling element 222 shown in FIG. 2, according to an aspect. As described previously when referring to FIG. 2, the downsample block down_2 (shown by 211) may be sequentially downsampled to the final downsample block "down_16" (shown by 214) via downsampling operations (shown by 222), as an example. Each downsampling operation 522 may perform 3D convolution and resolution reduction on each feature map, as an example.

As shown in FIG. 5, the input signal (down_2 in this example) may pass through two residual block modules "residual_block" 531. As will be described in further detail when referring to FIG. 7, the residual_block module 531 may perform 3D convolution on the input signal and output a normalized, transformed data tensor. This data tensor may pass through a max pooling function 535, as shown. The max pooling function 535 may be represented by the function "max_pool3d," which performs a max pooling operation for the 3D data. The max_pool3d function 535 will calculate the maximum value in each patch of the feature map of the input. The output of the max_pool3d function 535 will be a downsampled feature map that highlights the most present feature in the patch, allowing for extraction of complex image features. As shown previously in FIG. 2, the downsampling operation 522 may be performed sequentially for each resulting downsample block until the final downsample block (shown by 214 in FIG. 2) is obtained.

Figure 6:
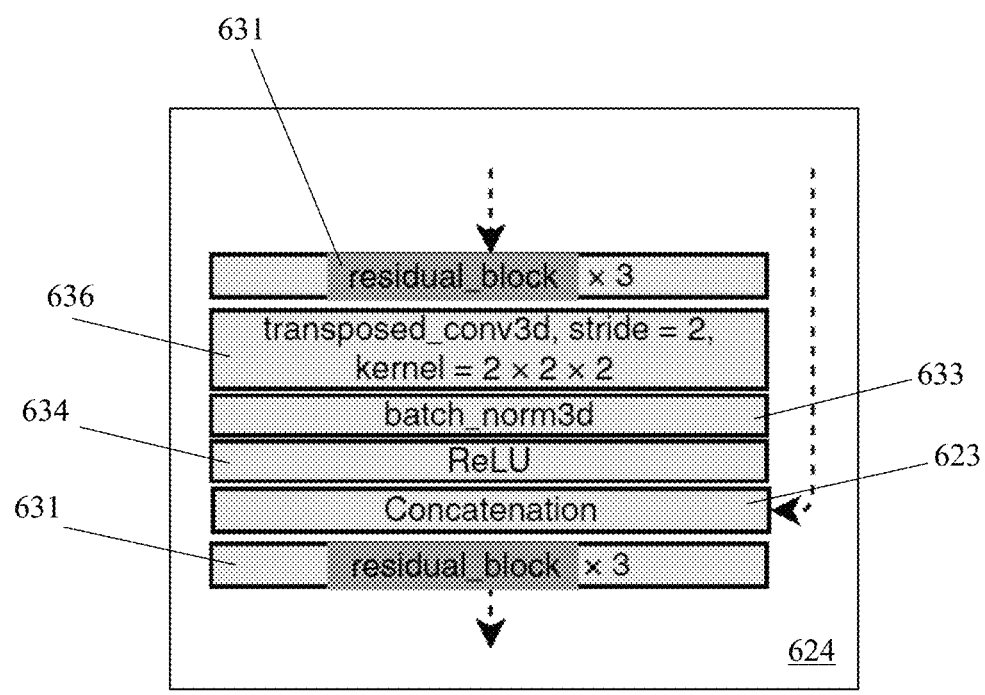
FIG. 6 is a flowchart illustrating the upsampling element 224 shown in FIG. 2, according to an aspect.

FIG. 6 is a flowchart illustrating the upsampling element 224 shown in FIG. 2, according to an aspect. As described previously when referring to FIG. 2, the final downsample block down_16 (shown by 214) may comprise the feature map defined by $$\left(1, 64, \frac{D}{16}, \frac{H}{16}, \frac{W}{16}\right),$$

as an example. The downsample block down_16 may be upsampled by upsampling element 624, resulting in the upsample block feature_map_8 (shown by 215 in FIG. 2) having a higher resolution.

As shown in FIG. 6, the downsample block down_16 may pass through a series of three residual_block modules 631 within the upsampling operation 624, as an example. As will be described in further detail in FIG. 7, each residual_block module 631 will perform a 3D convolution, batch normalization and piecewise linear operation on the input signal, as examples. The output of the series of residual_block operations 624 may then enter a transposed convolution module 636, which may be represented by the function "transposed_conv3d," as shown. As shown, the transposed convolution module 636 may be provided with stride and kernel input parameters. In this example, the stride parameter is set equal to 2 (two), which specifies two strides of convolution along each spatial dimension. The kernel parameter is set equal to 2×2×2, which specifies the depth, width, and height of the transposed convolution window, as an example. The transposed convolution module 636 increases the spatial resolution of the volume, resulting in an output tensor of the same size as the downsample input of the previous output. In other words, the transposed convolution operation 636 forms the same connectivity as the normal 3D convolution but in the backwards direction, as an example.

The output of the transposed convolution module 636 may then pass through a batch normalization module 636. As previously described when referring to FIG. 4, the batch_norm3d module 633 may perform batch normalization on the input, such that the mean of the input is close to 0 (zero) and the standard deviation is close to 1 (one), as an example. Following the batch_norm3d module 633, the data signal may pass through an activation function 634, which may be represented by the rectified linear activation unit ReLU. As discussed previously when referring to FIG. 4, ReLU 634 will apply a piecewise linear function over the input. As shown in FIG. 6, the output of the ReLU module 634 may then enter a concatenation module 623. Within the concatenation module 623, the convolved and transformed ReLU output is concatenated with the feature map of the same size from the corresponding downsample block "down_8" (shown by 213 in FIG. 2). As shown, the concatenated output of the concatenation module 623 may pass through a series of 3 residual_block modules 631, as an example. As similarly described when referring to FIG. 2, the output of the residual_block modules 631 may be the final feature map (shown by 215) defined by $$\left(1, 64, \frac{D}{8}, \frac{H}{8}, \frac{W}{8}\right),$$

as an example.

Figure 7:
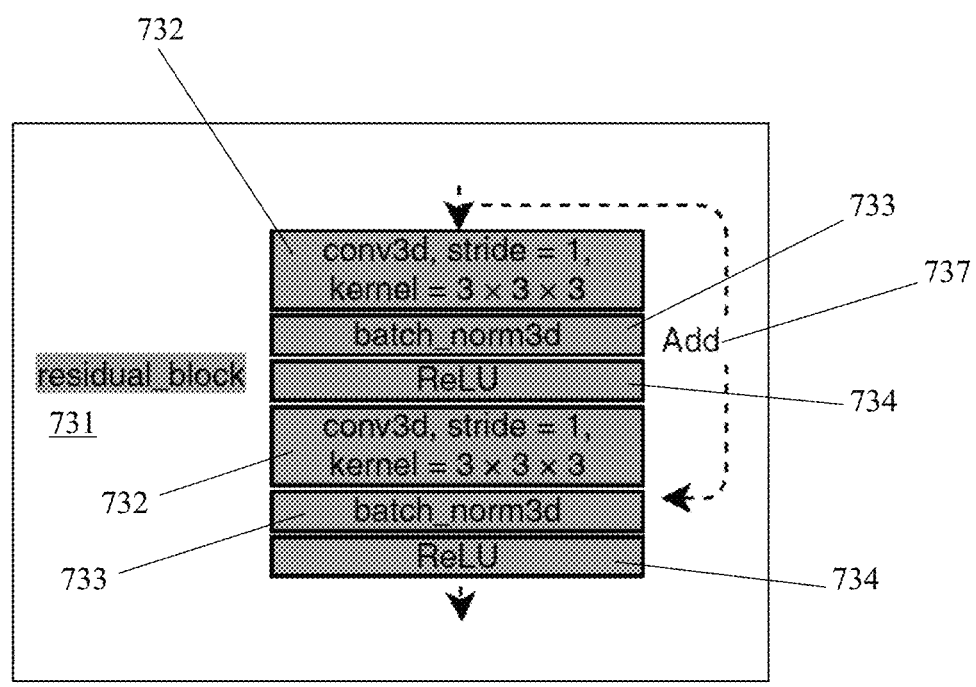
FIG. 7 is a flowchart illustrating the residual_block element 531 shown in FIGS. 5 and 6, according to an aspect.

FIG. 7 is a flowchart illustrating the residual_block element 531,631 shown in FIGS. 5 and 6, according to an aspect. As mentioned previously when referring to FIGS. 5 and 6, the residual_block element 731 may perform a 3D convolution, batch normalization and piecewise linear operation on the input signal. As shown in FIG. 7, the residual_block module 731 may comprise a number of submodules that function in a successive manner.

As shown in FIG. 7, the input signal may enter a first 3D convolution module 732 with input parameters stride and kernel. As shown, the stride parameter is set equal to 1 (one) to specify one stride of convolution along each spatial dimension, as an example. The kernel parameter is set equal to 3×3×3 to specify the three-dimensional volume of the convolution window, as an example. The convolution module 732 creates a convolution kernel that is convolved with the convolution layer input to produce a tensor of outputs. As shown, the output tensor may then pass into a batch normalization module 733, which can be represented by the function "batch_norm3d." As mentioned previously above, the batch normalization module 733 will normalize each plane in the input tensor. The normalized data signal may then pass through an activation function ReLU 734, as shown, to transform the summed weighted input signal into an activation output, as an example.

The output of the activation function 734 may then pass through a second 3D convolution module 732, as shown. The second convolution module 732 may perform identical operations as the first convolution module of the residual_block 731 and may include the same values for the input parameters stride and kernel, as shown as an example. The convolved output of the second 3D convolution module 732 may pass into a second batch normalization module 733. As shown, the feature map inputted to the residual_block 731 may be added 737 to the convolved signal, such that the input to the second batch_norm3d module 733 is the sum of the two signals. The output of the batch normalization module 733 may pass into a final activation function 734, such that the output of the residual_block 731 is a convolved, normalized and transformed signal containing the extracted features of the input feature map.

Figure 8:
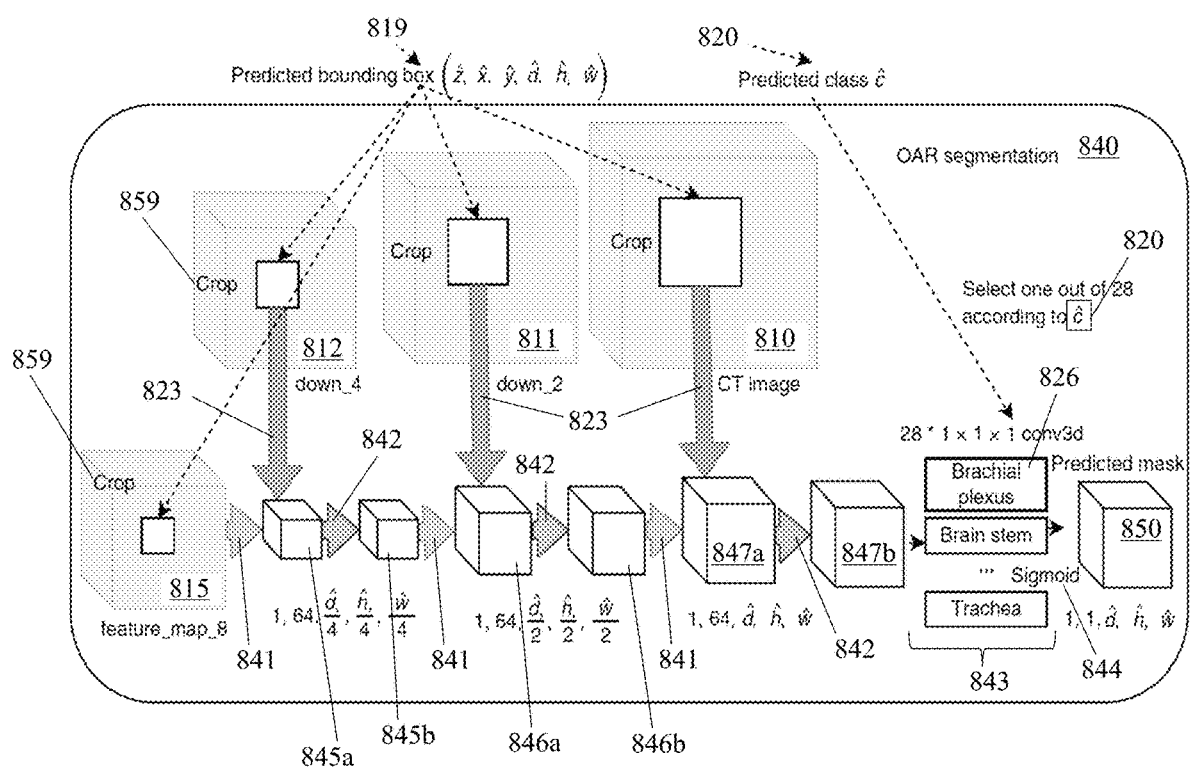
FIG. 8 is a flowchart illustrating an OAR Segmentation Network of the two-stage deep learning OAR delineation framework, according to several aspects.

FIG. 8 is a flowchart illustrating an OAR Segmentation Network 840 of the two-stage deep learning OAR delineation framework, according to several aspects. As mentioned previously above, the two-stage deep learning OAR delineation framework disclosed herein may be provided with two networks. The OAR Detection Network (illustrated in FIG. 2) may operate during the first stage of the deep learning OAR delineation framework. As described above, the OAR Detection Network outputs feature maps of fixed sizes describing detected OAR candidates. These feature maps, defined by bounding box regressions (shown by 319 in FIG. 3), and their corresponding class classification (shown by 320 in FIG. 3) may be passed into the OAR Segmentation Network 840 during the second stage of the deep learning OAR delineation framework. The OAR Segmentation Network 840 may segment each of the OAR regions (319) detected by the Detection Network and may produce a binary mask 850 delineating each OAR in the original image resolution.

As shown in FIG. 8, the OAR Segmentation Network 840 may take Predicted bounding boxes 819 as input, with each Predicted bounding box 819 comprising a rectangular cuboid defined by the coordinates $(\hat{z}, \hat{x}, \hat{y}, \hat{d}, \hat{h}, \hat{w})$. As shown, the OAR Segmentation Network 840 takes the feature_map_8 815 (shown previously by 215 in FIG. 2) and may crop 859 the extracted image features according to the Predicted bounding box 819. As an example, the feature_map_8 815 image features may be cropped 859 according to location, specified by $(\hat{z}, \hat{x}, \hat{y})$, and size, specified by $(\hat{d}, \hat{h}, \hat{w})$, of the Predicted bounding box 819. Upon cropping of the input feature map 815, the cropped feature map may be subsequently upsampled through a sequence of upsampling blocks 845-847, as shown.

As shown in FIG. 8, the cropped feature map may pass through a trilinear upsample 841, which will be discussed in more detail when referring to FIG. 9, resulting in a first upsample block 845a. As shown, the first upsample block 845a may be concatenated 823 with cropped image features from the feature map derived by the downsample block "down_4" 812. As an example, the down_4 feature map 812 may be cropped 859 according to the location $(\hat{z}, \hat{x}, \hat{y})$ and size $(\hat{d}, \hat{h}, \hat{w})$ of the Predicted bounding box 819, and concatenated 823 into the feature map of the corresponding upsample block 845a. The concatenated upsample block 845a may then pass through a 3D convolution and normalization step (shown in FIG. 10) 842, resulting in a convolved upsample block 845b with a feature map defined by $$\left(1, 64, \frac{\hat{d}}{4}, \frac{\hat{h}}{4}, \frac{\hat{w}}{4}\right),$$

as an example.

As shown in FIG. 8, the upsample block 845b may pass through another trilinear upsample 841, resulting in a third upsample block 846a. As shown, the third upsample block 846a may be concatenated 823 with cropped image features from the feature map derived by the downsample block "down_2" 811. As an example, the down_2 feature map 811 may be cropped 859 according to the location $(\hat{z}, \hat{x}, \hat{y})$ and size $(\hat{d}, \hat{h}, \hat{w})$ of the Predicted bounding box 819, and concatenated 823 into the feature map of the corresponding upsample block 846a. The concatenated upsample block 846a may then pass through a 3D convolution and normalization step 842, resulting in a convolved upsample block 846b with a feature map defined by $$\left(1, 64, \frac{\hat{d}}{2}, \frac{\hat{h}}{2}, \frac{\hat{w}}{2}\right),$$

as an example.

As shown in FIG. 8, the upsample block 846b may pass through a last trilinear upsample 841, resulting in a fifth upsample block 847a. As shown, the fifth upsample block 847a may be concatenated 823 with cropped image features from the feature map derived by the original CT input image 810. As an example, the CT image feature map 810 may be cropped 859 according to the location $(\hat{z}, \hat{x}, \hat{y})$ and size $(\hat{d}, \hat{h}, \hat{w})$ of the Predicted bounding box 819, and concatenated 823 into the feature map of the corresponding upsample block 847a. The concatenated upsample block 847a may then pass through a final 3D convolution and normalization step 842, resulting in a final segmentation upsample block 847b with a feature map defined by $(1, 64, \hat{d}, \hat{h}, \hat{w})$, as an example. As shown, the final segmentation feature map 847b consists of 64 channels with the same size dimensions $\hat{d} \times \hat{h} \times \hat{w}$ as the Predicted bounding box 819.

Finally, as shown, a 1×1×1 3D convolution 843 may be applied to the final feature map 847b. The 1×1×1 3D convolution 843 is chosen according to the Predicted class label $\hat{c}$ 820, as shown an example. As shown as an example, the Predicted class label $\hat{c}$ 820 corresponds to one of 28 possible OARs (e.g., Brachial plexus 826). Following the 1×1×1 3D convolution 843, a sigmoid transformation 844 may be applied to the final segmentation feature map to generate the Predicted binary mask 850. The Predicted mask 850 may be represented by m, a set indexed by voxel coordinates, and may comprise a feature map defined by $(1, 1, \hat{d}, \hat{h}, \hat{w})$, as an example. Upon comparison with the original input CT image shown in FIG. 2, a final binary mask $m^c$ delineates each OAR in the original image resolution D×H×W, as an example.

As mentioned previously, the Predicted mask m may be represented as a set indexed by voxel coordinates, with $m_i$ denoting the probability of a given voxel i being the foreground of the OAR. The same procedure outlined above may be applied to each detected OAR within a given CT scan input. The final predicted mask $m^c$ associated with a given OAR c is taken to be the union of all $m_i$ whose predicted OAR class label is c, as an example. Thus, an advantage of the OAR Segmentation Network 840 may be that the 3D prediction map containing all delineated OARs is outputted on the original 3D CT input image in the original image resolution.

Figure 9:
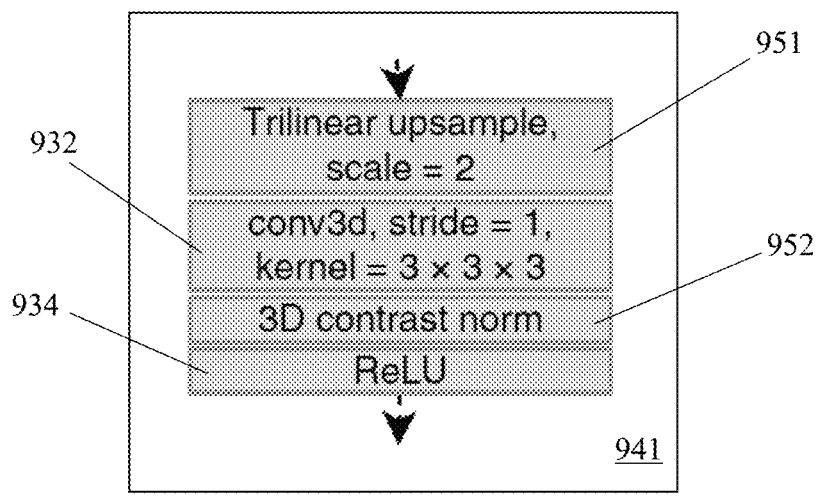
FIG. 9 is a flowchart illustrating the trilinear upsampling element 841 shown in FIG. 8, according to an aspect.

FIG. 9 is a flowchart illustrating the trilinear upsampling element 841 shown in FIG. 8, according to an aspect. As shown, the trilinear upsampling step 941 may comprise a sequence of submodules that function in a successive manner. As described previously when referring to FIG. 8, the cropped image features of each subsequent feature map in the OAR Segmentation Network may pass through the trilinear upsampling module 941 and undergo trilinear interpolation and 3D convolution, as an example.

As shown in FIG. 9, the cropped image features may enter a Trilinear upsample module 951. As shown, the Trilinear upsample module 951 may be provided with a "scale" parameter, which is set equal to 2 (two) in this example. The Trilinear upsample module 951 calculates values placed between existing voxel values by linearly weighting the eight closest neighboring values and scales the values by 2, according to the specified scale parameter. The output of the Trilinear upsample module 951 is an upsampled tensor that may then pass through a 3D convolution module 932, as shown. The 3D convolution module 932 may be provided with input parameters stride and kernel, as shown. As examples, the stride parameter specifies one stride of convolution along each spatial dimension and the kernel parameter specifies a 3×3×3 parameterized surface representation for the 3D convolution window. The convolved output tensor may then pass through a 3D contrast normalization module 952, as shown.

The 3D contrast normalization module 952 shown in FIG. 9 may help facilitate training of the segmentation module (shown by 840 in FIG. 8) and delineate anatomies with low CT image contrast. Referred to as 'local contrast normalization,' the contrast normalization step 952 may be applied to feature maps of the upsampling blocks. Local contrast normalization standardizes each 3D response map to zero mean and unit variance across all voxels. As an example, let $x \in \mathbb{R}^{C \times D \times H \times W}$ be a feature map with C channels and of dimension D×H×W. The local contrast normalization step 952 may transform the feature map x to $y \in \mathbb{R}^{C \times D \times H \times W}$ with $$y_{cijk} = \frac{x_{cijk} - \mu_c}{\sqrt{\sigma_c^2 + \epsilon}} \quad (A)$$

where $\mu_c$ and $\sigma_c$ are the mean and standard deviation of the voxel intensities, respectively, within the cth channel of the feature map x. The local contrast normalization step 952 can not only facilitate the training of the segmentation module (FIG. 8) by making the module converge faster but may also improve segmentation accuracy. Thus, an advantage of local contrast normalization may be the ability of the system to adapt to different contrasts in the image when segmenting different organs. An additional advantage may be the significant reduction in time spent by a clinician manually delineating OARs in a 3D CT image, as an example.

As shown in FIG. 9, the transformed feature map output of the contrast normalization module 952 may lastly pass through an activation function 934. The activation function 934 may be represented as a rectified linear activation unit "ReLU" which applies a piecewise linear function on the module input. The ReLU function 934 will output the input value directly if the value is positive, otherwise, the function 934 will output 0 (zero), as an example. The output of the activation function 934 will thus be a transformed upsampled feature map (e.g., upsample block 845a in FIG. 8).

Figure 10:
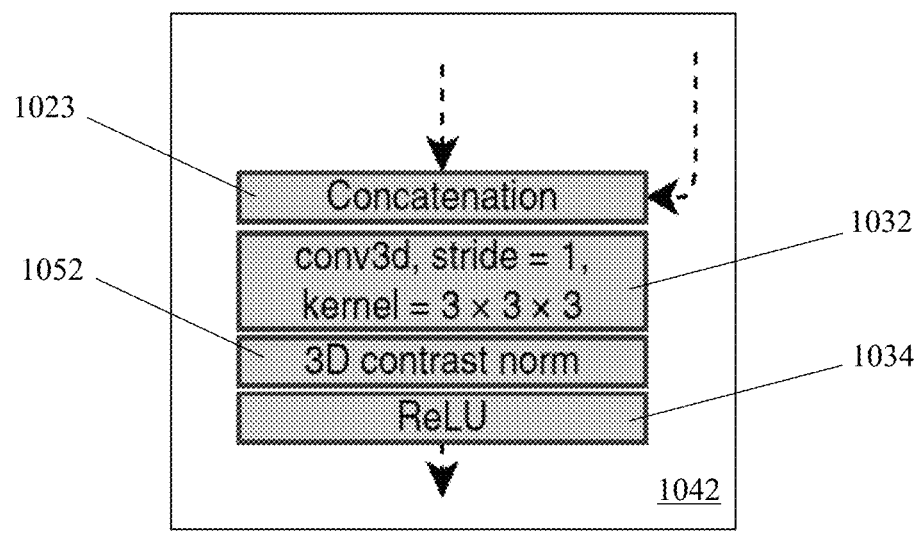
FIG. 10 is a flowchart illustrating the convolution and normalization element 842 shown in FIG. 8, according to an aspect.

FIG. 10 is a flowchart illustrating the convolution and normalization element 842 shown in FIG. 8, according to an aspect. As described previously when referring to FIG. 8, each upsample block (e.g., 845a) may undergo concatenation with a cropped feature map derived from a corresponding downsample block (e.g., 812), as well as convolution and normalization. As shown in FIG. 10, the two feature maps of equal dimension may enter the convolution and normalization stage 1042 and undergo 3D convolution and contrast normalization, as will be discussed herein below.

As shown in FIG. 10, two feature maps of equal dimension may first be concatenated via a concatenation module 1023. As described previously above, an upsample block (e.g., 845a) may be linked in a series with the cropped feature map of a corresponding downsample block (e.g., 812). The concatenated feature map may enter a convolution module 1032, which performs a 3D convolution on the map. As previously described above, the stride parameter specifies one stride of convolution along each spatial dimension and the kernel parameter specifies a 3×3×3 volume window for convolution. The convolved output of the convolution module 1032 may pass through a contrast normalization step 1052, as shown. As described previously when referring to FIG. 9, the local contrast normalization step 1052 standardizes the feature map to zero mean and unit variance across all voxels, as an example.

As shown in FIG. 10, the transformed feature map output of the contrast normalization module 1052 may lastly pass through an activation function 1034. As described previously when referring to FIG. 9, the ReLU activation function 1034 may apply a piecewise linear function on the input, as an example. The output of the activation function 1034 will thus be a transformed concatenated feature map (e.g., upsample block 845b in FIG. 8).

Figure 11:
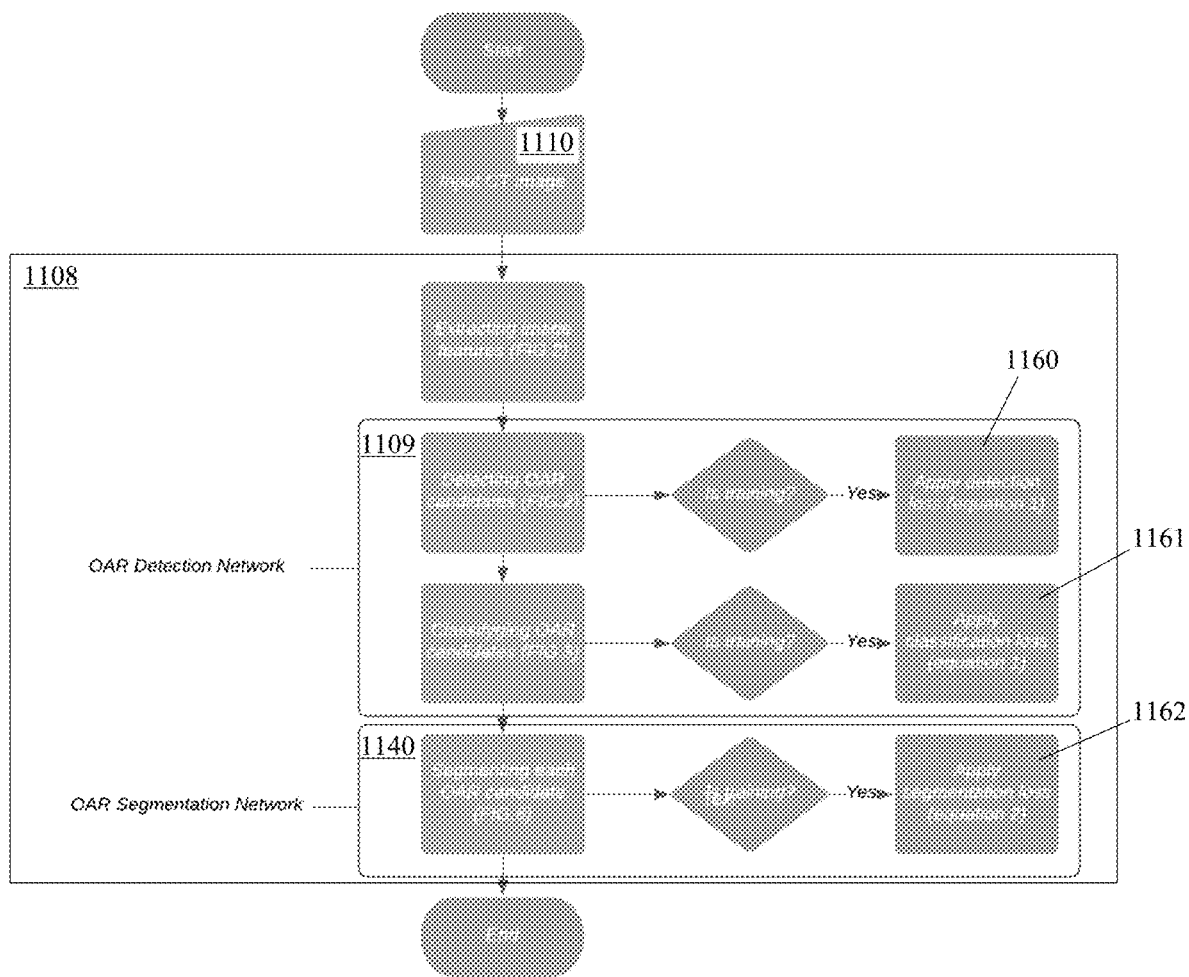
FIG. 11 is a flowchart illustrating a method of training the two-stage deep learning OAR delineation framework, according to an aspect.

FIG. 11 is a flowchart illustrating a method of training the two-stage deep learning OAR delineation framework, according to an aspect. As mentioned herein above, the OAR delineation framework 1108 may be provided with a training method and training data that enable the framework to accurately and efficiently delineate OARs in medical images. As shown as an example in FIG. 11, the disclosed training method may train the two-stage OAR delineation framework 1108 end to end, which trains the OAR Detection Network 1109 and OAR Segmentation Network 1140 successively.

As shown in FIG. 11, the method of training the OAR delineation framework 1108 may be provided with training data in the form of an input CT image 1110, as an example. As described previously above when referring to FIG. 2, the input CT image 1110 may undergo feature extraction and pass through the OAR Detection Network 1109. As previously shown in FIG. 2, the feature extraction results in a final feature map associated with the input image 1110, which may be accomplished by passing the input image 1110 through a series of downsampling blocks (211-214) that encode the image features. OAR candidates within the final feature map may then be detected, as shown. In order to train the OAR Detection Network 1109 to detect OAR candidates, a detection loss function 1160 may be applied, which will be discussed in further detail herein below.

As an example, let $t_i \in \mathbb{R}^6$ be the bounding box parameter associated with the ith anchor, predicted by the bounding box regression head (227 in FIG. 2), and $P_i$ be the probability of the anchor being an OAR, predicted by the binary classification head (228 in FIG. 2). A multi-task loss function allows having multiple tasks, box regression (229) and classification (230) in this case and brings the individual losses of the tasks to the same scale. The detection multi-task loss function $\mathcal{L}_d$ may be minimized (i.e., uncertainty may be minimized) such that $$\mathcal{L}_d(\{P_i\}, \{t_i\}) = \frac{1}{N_{cls}} \sum_i \mathcal{L}_{cls}(P_i, P_i^*) + \lambda \frac{1}{N_{reg}} \sum_i \mathcal{L}_{reg}(t_i, t_i^*) \quad (1)$$

where the first term is a classification loss, the second term is a regression loss and λ is a hyper parameter. The hyper parameter λ may be set equal to 1 to balance the classification and regression losses in this case. $N_{cls}$ and $N_{reg}$ may be the total number of anchors included in the classification and regression loss calculation, respectively. In this example, $P_i^*$ is 0 if the ith anchor does not contain any of the 28 OARs and 1 otherwise. $t_i^*$ is the ground truth box parameter, which measures the accuracy of the machine learning results against the training dataset. Both $t_i$ and $t_i^*$ may be parameterized relative to the size of the anchor box. Weighted binary focal loss is used for $\mathcal{L}_{cls}$ (classification loss function) and smooth $\ell_1$ loss for $\mathcal{L}_{reg}$ (regression loss function). The bounding box parameter (229) associated with the ith anchor and the probability (230) of the anchor being an OAR define the detected OAR candidates (shown previously by 316 in FIG. 3).

As shown in FIG. 11, the detected OAR candidates may then be classified, as discussed previously when referring to FIG. 3. As previously shown in FIG. 3, the feature map corresponding to detected OAR candidates may be ROI-pooled (317) and may pass through two FC layers (318) to classify the OAR candidates according to one of 28 possible OARs, as an example. In order to train the OAR Detection Network 1109 to classify OAR candidates, a classification loss function 1161 may be applied, as an example. As was performed previously using equation (1), the classification multi-task loss function may be minimized to weigh the losses generated by each task. In reference to equation (1), $\mathcal{L}_{cls}$ (classification loss function) may be replaced by a weighted cross entropy loss of the 29 classes, while $\mathcal{L}_{reg}$ (regression loss) remains the same.

As shown, the detected OAR candidates and their classifications may pass into the OAR Segmentation Network 1140, as was discussed previously when referring to FIG. 8. As disclosed herein above, the OAR Segmentation Network 1140 may segment each of the OAR regions detected by the Detection Network 1109 and may produce a binary mask (850) delineating each OAR in the original image resolution. In order to train the OAR Segmentation Network 1140 to segment OAR candidates, a segmentation loss function 1162 may be applied, which will be discussed in further detail herein below.

As an example, the segmentation loss associated with one CT input scan 1110 may be defined to be $$\mathcal{L}_s = \Sigma_{c=1}^{28} I(c)(1-\phi(m^c, g^c)) \qquad (2)$$

where I(c) is an indicator function, taking the value of 1 (one) if OAR c is detected by the detection module 1109 and 0 (zero) otherwise. $g^c$ denotes the ground truth binary mask of OAR c, which measures the accuracy of the binary mask prediction against the learned training data. The ground truth binary mask is described as $g_i^c = 1$ if voxel i lies within the OAR and zero otherwise. $\phi(m, g)$ computes a soft Dice score between the predicted mask m and the ground truth g. The Dice score can be used to quantify how closely the OAR delineation framework matches the training dataset's manually delineated ground truth segmentation. The soft Dice score may be defined to be $$\phi(m, g) = \frac{\sum_{i=1}^{N} m_i g_i}{\sum_{i=1}^{N} m_i g_i + \alpha \sum_{i=1}^{N} m_i(1-g_i) + \beta \sum_{i=1}^{N}(1-m_i)g_i + \epsilon} \qquad (3)$$

where i is a voxel index and N denotes the total number of voxels. The terms $\Sigma_{i=1}^{N} m_i(1-g_j)$ and $\Sigma_{i=1}^{N}(1-m_i)g_i$ may be understood as soft false positives and soft false negatives, respectively. Parameters $\alpha$ and $\beta$ control the weights of penalizing false positives and false negatives, respectively, such that the false positive and false negative predictions may be reduced. Both parameters $\alpha$ and $\beta$ are set equal to 0.5 in this example. The $\epsilon$ term was added to equation (3) to ensure the numerical stability of the segmentation loss function. Thus, an advantage may be that the suppression of false positives and/or false negatives significantly reduces the amount of time needed to manually remove false positives from a resulting delineation map. An additional advantage may be the accurate delineation of all OARs in an input CT image 1110.

As shown in FIG. 11, equations (1) and (2) above may be implemented to measure and minimize the loss/error associated with detecting, classifying and segmenting OAR candidates. Upon completion of the training method disclosed herein above, the two-stage OAR delineation framework 1108 may accurately and efficiently delineate OARs present in 3D medical images 1110. The OAR delineation framework need only be trained with CT images of manually delineated OARs in the head and neck, thorax, and abdomen regions for the framework to automatically delineate OARs in these regions, respectively. Examples of the performance and test of the OAR delineation framework disclosed herein will be described in detail below.

FIGS. 12A-12H illustrate exemplary images in an example of use and test of the two-stage deep learning OAR delineation framework to delineate OARs 1256, according to several aspects. As shown as an example in FIGS. 12A-12D, the deep learning OAR delineation framework disclosed herein above may be particularly effective at accurately delineating OARs 1256 while running on a commodity GPU. As an example, a CT image of the head region 1210 (illustrated as an axial slice with a window width of 400 and a level of 35 in Hounsfield units) may be passed into the deep learning OAR delineation framework for image feature extraction and analysis. As described herein above, the sequence results in a final binary predicted mask (850) that delineates the OARs in the original image resolution, as an example. This segmentation process is completed for each OAR, resulting in a contour map 1250 delineating each OAR present in the original CT scan of the head region 1210, per the example.

Figure 12A:
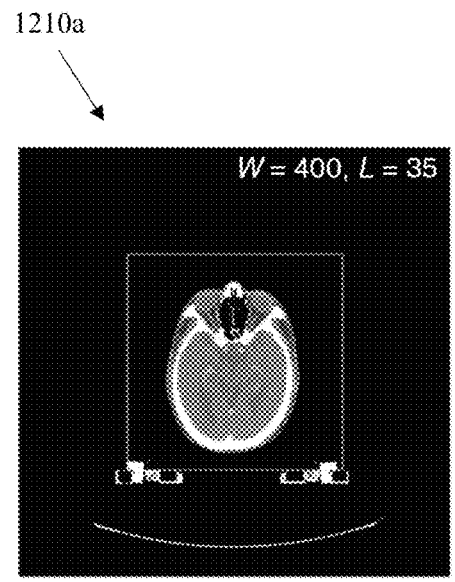
FIGS. 12A-12H illustrate exemplary images in an example of use and test of the two-stage deep learning OAR delineation framework to delineate OARs, according to several aspects.
Figure 12B:
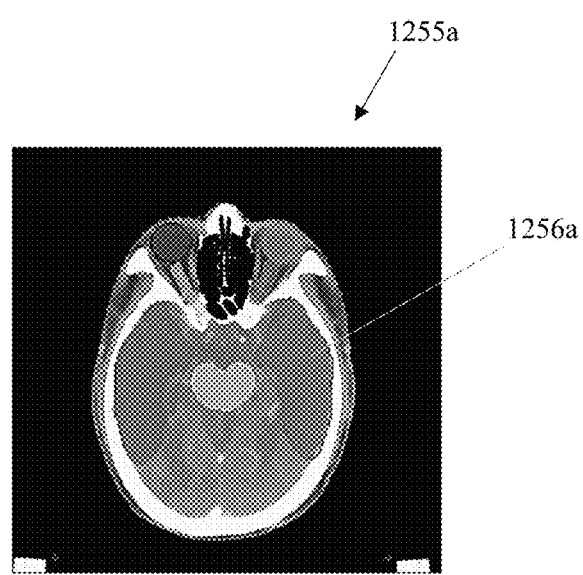
Figure 12C:
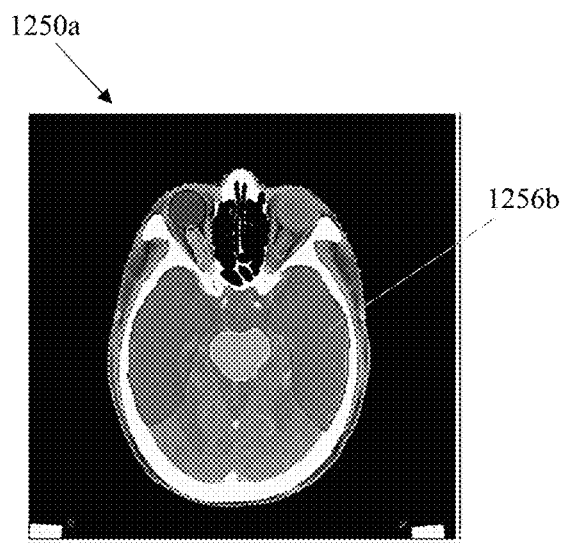
Figure 12D:
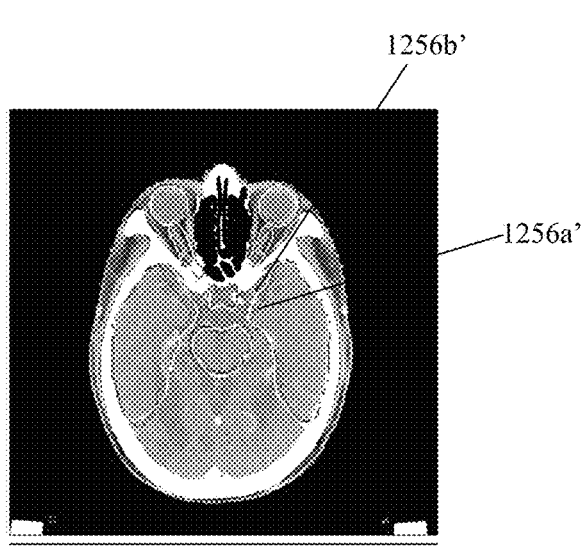

As shown as an example in FIG. 12C, the two-stage OAR deep learning OAR delineation framework may output a contour map 1250 transposed over the original CT scan delineating each OAR. FIG. 12B illustrates an example of a manual OAR delineation 1255 of the original CT scan 1210 performed by professional radiation oncologists. The manual delineation 1255 shown in FIG. 12B is an example of training data that may be used to train and test the OAR delineation framework to delineate OARs. FIG. 12D illustrates a comparison of each contour line produced by the OAR delineation framework against those of the manual delineation.

As an example, let the OAR delineation framework produce the contour map 1250 for the input CT scan 1210. The OAR delineation framework delineation 1256b of the left temporal lobe, as shown in FIG. 12C, may be compared to the manual delineation 1256a (FIG. 12B), as an example. As shown in FIG. 12D, the contour line 1256b', corresponding to the automatic delineation 1256b, visually showcases a similar shape, size and location to the contour line 1256a', corresponding to the manual delineation 1256a. As indicated by the visual comparison of all the contour lines in FIG. 12D, the OAR delineation framework may accurately output OAR delineations comparable to those delineated by the oncologists. Thus, an advantage of the deep learning OAR delineation framework disclosed herein may be the ability to feasibly delineate all 28 OARs from whole-volume CT images using only commodity GPUs.

Figure 12E:
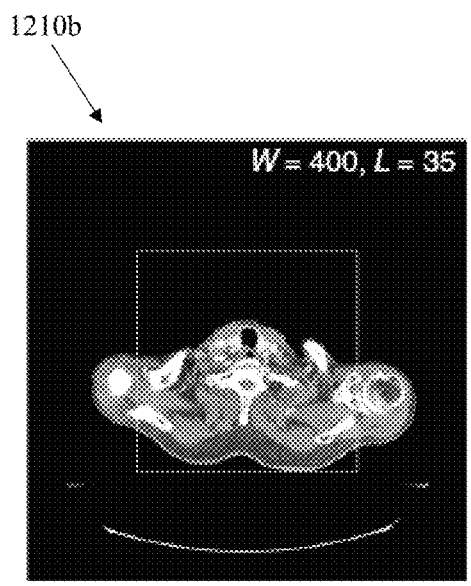
Figure 12F:
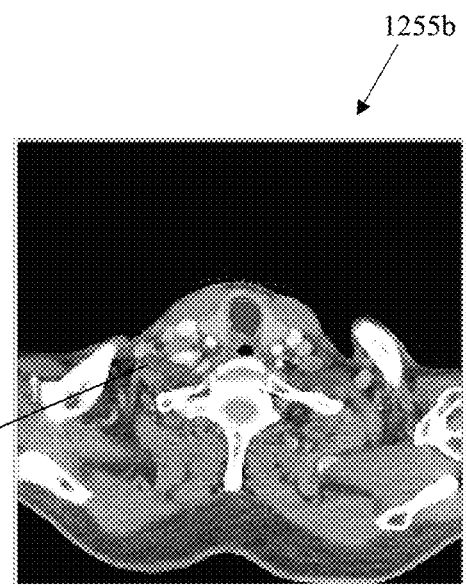
Figure 12G:
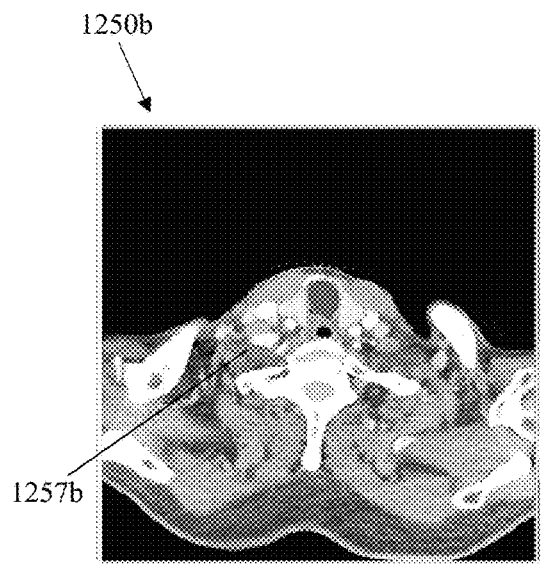
Figure 12H:
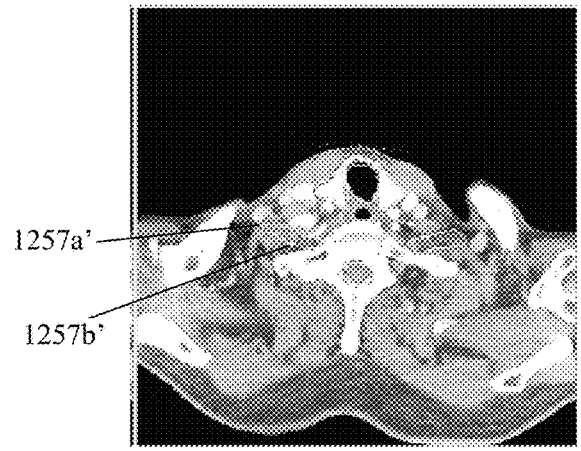

As shown as another example in FIGS. 12E-12H, the DCNN OAR delineation framework may delineate OARs present in a CT scan of the neck region. FIG. 12E illustrates an example CT scan 1210b of a patient's neck region. As an example, the CT scan 1210b may pass into the DCNN OAR delineation framework disclosed herein to segment OARs in the shown neck region. FIG. 12F shows a manual delineation 1255b of the CT scan 1210b, wherein, as an example, the brachial plexus 1257a has been delineated, as shown. FIG. 12G illustrates the output 1250b of the DCNN framework, wherein the same OAR (brachial plexus 1257b) has also been delineated. As shown as a comparison of the two delineations, FIG. 12H illustrates contour lines of the manual delineation 1257a' and the DCNN delineation 1257b'. As shown, the model's prediction 1250b in comparison to the oncologist's delineation 1255b again visually demonstrates the accuracy in the DCNN framework's performance.

While FIGS. 12A-12H visually demonstrate the OAR delineation framework's ability to perform well in comparison with manual OAR delineation performed by human experts, the OAR delineation framework disclosed herein above was also compared with classical and state-of-the-art computer methods. The classical method, known as multi-atlas segmentation, may segment OARs from cropped local patches by mapping to image templates. The state-of-the-art methods, such as AnatomyNet, may also utilize deep learning convolutional neural networks, but are prone to producing false positives because the models do not constrain the rough location and size of an OAR before segmentation. Furthermore, the methods may only process the 3D medical images incrementally in two-dimensional slices, as an example. As a result, the classical and state-of-the-art methods delineate OARs less accurately due to the loss of image features present in complex anatomies of organs in the body. The results of the comparisons can be found summarized in FIGS. 13-15, which will be described in greater detail below.

FIG. 13 is a table summarizing a Dice similarity coefficient comparison of the two-stage deep learning OAR delineation framework with current delineation methods, according to an aspect. As discussed above, the OAR Segmentation Network (shown by 840 in FIG. 8) results are represented by 28 binary masks, one for each OAR, as an example. Each binary mask is a 3D array of the same size as the input 3D medical images, with values of either 0 (zero) or 1 (one), indicating whether the underlying voxel is part of the corresponding OAR. The volumetric Dice similarity coefficient (DSC) measures the volumetric overlap between the predicted masks and correct masks (i.e., masks from manual delineation).

As an example, let $M_p$ and $M_g$ be the set of voxels with value 1 in the predicted and correct masks, respectively. The DSC may be defined as $$DSC = \frac{2|M_p \cap M_g|}{|M_p| + |M_g|},$$

measuring the volumetric overlap between the two masks. The DSC performance of the OAR delineation framework for delineation of each OAR can be shown in FIG. 13 under the column heading "$U_a$-Net" 1308. As shown in FIG. 13, the DSC on the test data was calculated for the performances of multi-atlas segmentation (MAS), AnatomyNet and oncologists (Human and Humana). In order to ensure consistent comparisons, the models were trained on the same training datasets using the same procedure.

As shown in Table 1 below, three datasets (e.g., Dataset 1, Dataset 2) were used to train and subsequently test the DCNN disclosed herein. Each dataset contains a number of real-world CT scans, where the CT scans come from a variety of sources and were taken on patients of diverse backgrounds. As shown in Table 1, Dataset 1 contains CT scans from the head and neck areas of patients and the delineation of OARs in each scan by radiation oncologists. The data include 175 CT scans from patients with head and neck cancer, as shown in Table 2, who undertook radiation therapy from 2016 to 2018. The CT scans were manually delineated by an experienced radiation oncologist, such that a clinically relevant set of 28 OARs were delineated in each CT scan, as shown. As shown, Dataset 2 consists of CT scans from two sources: Head-Neck Cetuximab (HNC) and Head-Neck-PET-CT (HNPETCT), both of which are publicly available. Lastly, Dataset 3 contains CT scans from a public dataset known as Public Domain Database for Computational Anatomy (PDDCA), as shown in Table 1.

TABLE 1

Datasets used in this study

| Data source | | No. of OARs annotated | Train | Test |
| --- | --- | --- | --- | --- |
| Dataset 1 | In-house | 28 | 145 | 30 |
| Dataset 2 | HNC | 28 | 18 | 17 |
| | HNPETCT | 28 | 52 | 53 |
| Dataset 3 | PDDCA | 9 | 33 | 15 |
| Total | | | 248 | 115 |

TABLE 2

Characteristics of the in-house collected data

| | Train | Test |
| --- | --- | --- |
| No. of patients (CTs) | 145 | 30 |
| Patient average age (years) | 61.0 | 65.5 |
| Gender | | |
| Male | 112 | 24 |
| Female | 33 | 6 |
| Tumour site | | |
| Nasopharynx | 25 | 7 |
| Hypopharynx | 14 | 7 |
| Larynx | 18 | 2 |
| Nasal cavity | 3 | 1 |
| Brain | 50 | 10 |
| Oropharynx | 7 | 1 |
| Parotid gland | 4 | 0 |
| Other | 24 | 2 |

The data consist of 175 CT scans randomly split to training and testing.

Of the 175 CT scans in Dataset 1 (shown in Table 1), 145 were used to train the various models shown in FIG. 13 and 30 scans were used to test them. As shown in FIGS. 13 and 14, the bold numbers in each column represent the best results. As shown in FIG. 13, in terms of DSC, $U_a$-Net 1308 outperformed AnatomyNet in 27 out of 28 OARs, with an average improvement of 4.24% on Dataset 1. $U_a$-Net performed particularly better on anatomies that may be difficult to delineate under normal contrast conditions, such as the optic chiasm 1370 and sublingual gland 1371, as shown as an example. This improvement in delineation of organs with complex anatomies may be attributed to the local contrast normalization mechanism implemented in the OAR Segmentation Network (discussed previously when referring to FIG. 9). As shown, $U_a$-Net 1308 performed slightly worse than AnatomyNet on the right ear (Ear R) 1369, however, the difference is relatively small and may be neglected. As compared to MAS, $U_a$-Net generated even higher scores, as shown in FIG. 13 as an example. In terms of DSC, $U_a$-Net 1308 performed about 15.56% better than MAS for all OARs, which further indicates that the classical computer method may not be as competitive as the deep learning-based methods ($U_a$-Net and AnatomyNet).

As shown in FIG. 13, the performance of $U_a$-Net 1308 was also compared to manual OAR delineation performed by human experts. An experienced radiation oncologist manually delineated the 28 OARs on the 30 CT scans in the test set from Dataset 1 in accordance with the normal professional procedure, but without consulting other professionals or seeking assistance from additional sources such as MRI images. As shown, in terms of DSC, $U_a$-Net 1308 outperformed the human expert on 27 out of 28 OARs, with an average improvement of 10.15%. The human expert's delineation (represented by Human) had the lowest DSC scores on optic chiasm 1370 (28.61), brachial plexus 1372 (33.03) and sublingual gland 1371 (35.16), which are small in size and have relatively low contrast in CT images, thereby highlighting the advantage of utilizing a deep learning-based method as a delineation tool.

In real clinical practice, as an example, clinicians may also reference MRI images during the delineation process. To benchmark the delineation quality of clinicians in a real clinical setting, the same clinician updated the delineation results using inputs from both CT and MRI images as guides. This update led to an increase of the average DSC to 72.17% (represented by Humana). As shown in FIG. 13, $U_a$-Net 1308 still outperformed the oncologist on 26 out of 28 OARs, a resounding majority. Thus, an advantage of the deep learning OAR delineation framework may be the ability of the framework to be implemented and perform efficiently in a real clinical setting.

FIG. 14 is a table summarizing a Hausdorff distance comparison of the two-stage deep learning OAR delineation framework with current delineation methods, according to an aspect. In addition to the DSC, the Hausdorff distance (HD) was measured between the boundaries of the predicted and correct masks for each method. As an example, the HD measures the distance between two contours (illustrated previously in FIGS. 12D and 12H); for purposes of comparing the models, a smaller HD distance represents a more accurate model. Let $C_p$ and $C_g$ denote the contours of the predicted and correct masks, respectively. Let max HD be defined as $\max\{h(C_p, C_g), h(C_g, C_p)\}$, where $h(C_p, C_g) = \max_{a \in C_p} \min_{b \in C_g} \|a-b\|$. Because max HD is very sensitive to outliers, a more commonly used metric, 95% HD, which measures the $95^{th}$ percentile distance between two contours, is used instead, in this example.

As similarly described when referring to FIG. 13, the state-of-the-art models were trained on the same training Dataset 1 using the same procedure, and the performance of each model in terms of their 95% HD were compared and tabulated, as shown in FIG. 14. As shown, the advantage of $U_a$-Net 1408 over AnatomyNet is even more obvious when evaluated in terms of the HD, with the average 95% HD decreasing from 21.96 mm to 6.21 mm, in this example. As shown, AnatomyNet is prone to produce false positives outside the normal range of OARs, which is expected because its segmentation is performed on whole-volume images instead of localized OAR regions (as in $U_a$-Net). These false positives were small in terms of the number of voxels, significantly increasing the HD. Similarly, $U_a$-Net 1408 outperformed MAS in terms of the 95% HD on all but one OAR (spinal cord 1472). However, the difference between the reported distances is relatively small, which may still render $U_a$-Net a superior model overall.

As shown in FIG. 14, the performance of $U_a$-Net 1408 was also compared to manual OAR delineation performed by human experts. The gap between the human expert (Human and Humana) and the deep learning model delineation was smaller when the results were evaluated using the HD. As shown, $U_a$-Net performed better than the human expert (with smaller 95% HD) on most of the OARs (22 out of 28), lowering the average 95% HD from 8.01 mm to 6.28 mm (a 21% reduction). Because the HD is very sensitive to outliers, the HD was a more challenging metric for models than human experts, whose mistakes were mostly confined to regions around OARs.

It should be noted that the comparisons of the DSC and HD for $U_a$-Net and the other models shown in FIGS. 13 and 14 were also made for Datasets 2 and 3 listed in Table 1. Like the comparison results shown in FIGS. 13 and 14, the DSC and HD comparisons based on Datasets 2 and 3 illustrated the advantage and superiority of the OAR DCNN disclosed herein. The tabulated results shown in FIGS. 13 and 14 are shown for exemplary purposes and are not meant to suggest the success of the DCNN based solely on Dataset 1. As an example, the DCNN model was compared to results taken from state-of-the-art computer models obtained on Dataset 3 (PDDCA). These state-of-the-art models reported delineation results evaluated in terms of DSC on nine OARs from the Dataset 3 test set. For this comparison, $U_a$-Net obtained the best delineation results on eight out of nine OARs, achieving an average DSC score of 81.23% across the nine OARs, higher than all previous methods.

FIG. 15 is a table summarizing an exemplary time comparison for an oncologist delineating OARs with and without assistance from the two-stage OAR delineation framework, according to an aspect. In order to demonstrate the two-stage OAR delineation framework's clinical utility, a comparison of the time spent by radiation oncologists delineating OARs under two modes was conducted. In the first mode (Mode 1), the delineation was performed completely manually according to normal professional procedure. In the second mode (Mode 2), the delineation results of all 28 OARs from the OAR delineation framework were provided to the clinician, who would then verify the results and revise incorrect delineations when necessary. As shown in FIG. 15 as an example, the overall work time in this case includes the time spent on verifying the results, as well as the time spent on modifying the model's predictions.

As an example, ten new CT scans 1573 of the head and neck regions from real-life radiotherapy planning were studied. The time spent by an experienced radiation oncologist to delineate 28 OARs in each of the ten cases 1573 (PA1-PA10) was recorded, as shown in FIG. 15, operating under the two modes described above. All delineation results were checked and verified by a second radiation oncologist to ensure the quality of delineation, as an example.

As shown in FIG. 15, without assistance from the deep learning delineation model, the radiation oncologist spent on average 33.6±2.55 minutes (min) 1576 to delineate one case. By contrast, when assisted by the deep learning delineation model, the delineation time was substantially reduced, resulting in an average value of 13.1±3.14 min 1577, representing an approximately 61% reduction in time, as shown. As shown for the example, a paired t-test confirmed that the differences 1575 (on average 21.68 min) between the two modes were statistically significant 1574 ($P=4.5\times 10^{-9}$).

Altogether, the experimental results described above and shown in FIGS. 12-15 suggest that the two-stage OAR delineation framework implemented as $U_a$-Net is beneficial for improving the performance of deep learning models in terms of DSC, and substantially so in terms of the HD. Additionally, the two-stage delineation framework disclosed herein may be capable of providing better delineation performance than human experts. It should be noted that the model can complete the entire delineation process of a 3D medical image within a couple seconds. By contrast, the human expert took, on average, 34 minutes to complete one case, highlighting the significant advantages of the DCCN OAR delineation framework. When offered as a tool to assist clinicians' manual delineation of OARs, the deep learning model can generalize well on previously unseen cases and can save a clinician's time by as much as 61%, as an example.

As described herein above, the OAR DCNN may automatically and accurately delineate OARs present in 3D CT scans. In clinical settings, these 3D CT scans may be taken of the upper half of the body, such that all organs can be viewed in a single scan at one time. As such, a single CT scan may include the head and neck, thorax and abdomen regions of the body, for example, requiring a clinician or radiation oncologist to separate and categorize the individual regions present in this CT scan before delineating OARs in each region. Thus, it may be advantageous to provide the OAR delineation framework disclosed herein with a method of automatically detecting and separating regions of the body present in 3D CT scans.

Figure 16:
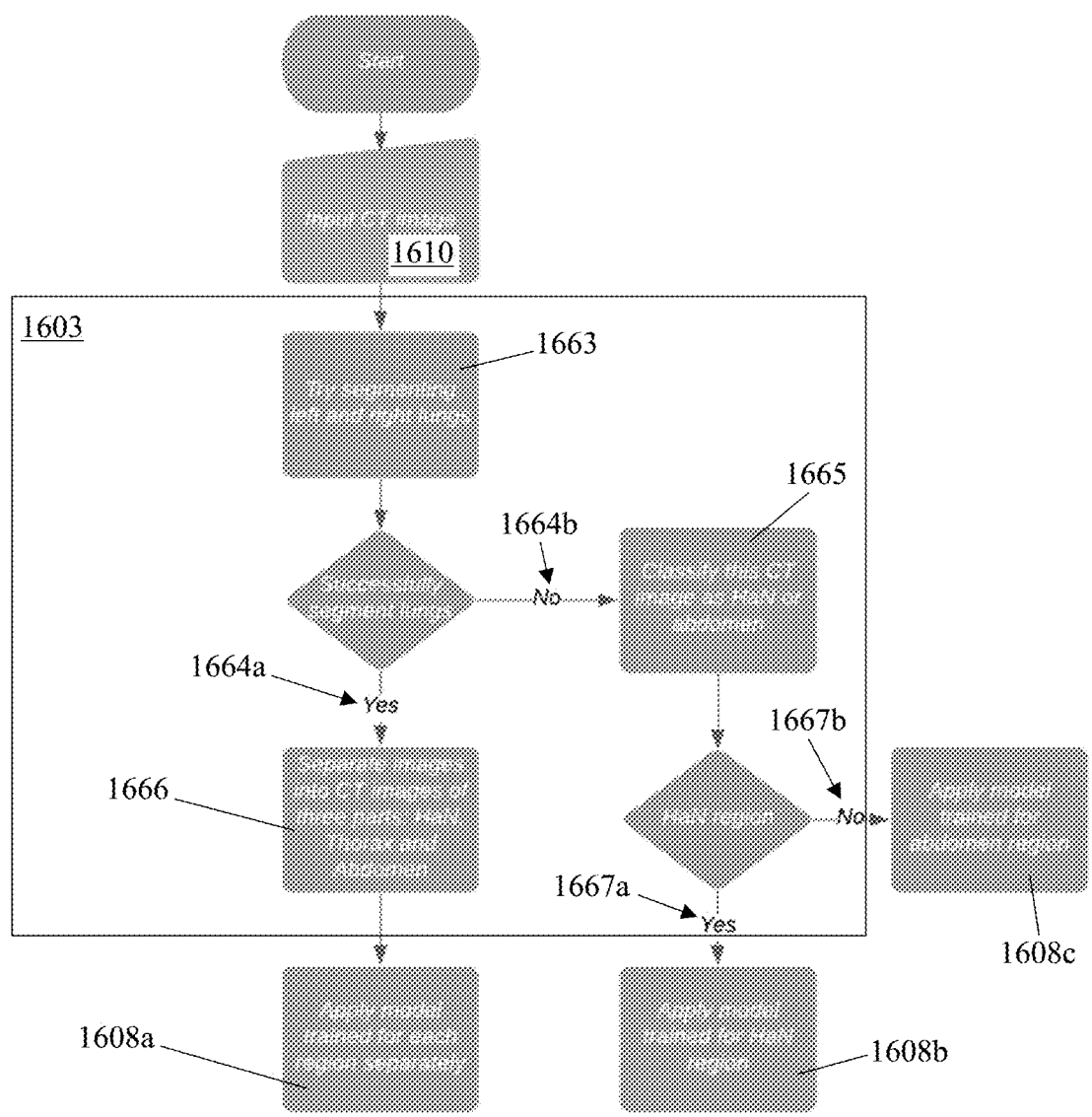
FIG. 16 is a flowchart illustrating a method of detecting and separating regions in whole-volume medical images for OAR delineation, according to an aspect.

FIG. 16 is a flowchart illustrating a method of detecting and separating regions in whole-volume medical images 1610 for OAR delineation, according to an aspect. The region separation method may be provided with a region detection model 1603, as shown in FIG. 16. As an example, the region detection model 1603 may be provided with a segmentation algorithm 1663, a separation algorithm 1666 and a classification algorithm 1665 to automatically separate the different organ-containing regions (e.g., thorax and abdomen) of the body that may be present in a whole-volume input scan 1610.

As shown in FIG. 16, an input CT image 1610 may pass into the region separation model 1603 to automatically separate organ-containing regions present in the CT image 1610. The input CT image 1610 may pass through a segmentation algorithm 1663 that attempts to segment left and/or right lungs in the CT image 1610, as shown as an example. The segmentation algorithm 1663 segments lungs from the CT image using a two-dimensional slice by slice approach, which will be discussed in further detail when referring to FIG. 17. The segmentation algorithm includes a convolutional neural network that may be trained using a well-known classification algorithm (e.g., AlexNet). The result of the segmentation algorithm 1663 will be a segmentation mask of the same shape and size as the original CT input image 1610. If the algorithm successfully segments lungs (shown at 1664) from the CT image 1610, the region containing the lungs will be identified as the thorax (i.e., chest) region, as an example. Otherwise, the CT image must only contain a single region of the body, specifically either the head and neck ("HaN" in FIG. 16) or abdomen region.

As shown, if the lungs are successfully segmented (shown at 1664a) from the CT image 1610, the segmentation mask resulting from the segmentation algorithm 1663 may pass into a separation algorithm 1666. As described above, the 2D slices containing lung segmentation define the thorax region, as an example. For identification purposes, the region spatially located above the top of the lungs in the CT scan 1610 may be considered the head and neck region. The region spatially located below the bottom of the lungs in the CT scan 1610 may be considered the abdomen region. The separation algorithm 1666 may add about 5 cm to both the top and bottom of the thorax region when separating the CT image into the three regions, as an example, which will be discussed when referring to FIGS. 19A-19B. As shown in FIG. 16, the OAR delineation framework disclosed herein above may be applied (1608a) to each of the three regions outputted from the region detection model 1603 to separately delineate OARs in the head and neck, thorax, and abdomen regions, as an example. It should be understood that the OAR delineation framework will be specifically trained to delineate OARs in a specific region, such that three OAR delineation frameworks may operate simultaneously to delineate OARs in all three regions of a given CT image, as an example.

As shown in FIG. 16, if the segmentation algorithm 1663 fails to successfully segment the lungs (shown at 1664b) from the input CT image 1610, there is no thorax region present in the CT image 1610. Thus, the CT image 1610 may only be of the head and neck or abdomen region. As shown, the CT image 1610 may then pass through a classification algorithm 1665 to classify (i.e., identify) the CT image as being of either the head and neck or abdomen region. The classification algorithm 1665 may be trained to predict the correct class of the input CT images slice by slice. A binary classifier (CNN) in the classification algorithm 1665 may predict each 2D slice as either being the head and neck region or the abdomen region, which will be discussed in further detail when referring to FIG. 18. Then, if more than 50% of the 2D slice predictions are for the head and neck region, the current CT image may be classified as being of the head and neck region. As shown in FIG. 16, each detected region can later be passed into an OAR delineation framework to delineate OARs in that region. For example, a CT image determined to be of the head and neck region (shown at 1667a) may be passed into an OAR delineation framework trained to delineate OARs in the head and neck region (shown at 1608b). The same is true for the abdomen region, as shown in FIG. 16 (1608c).

Figure 17:
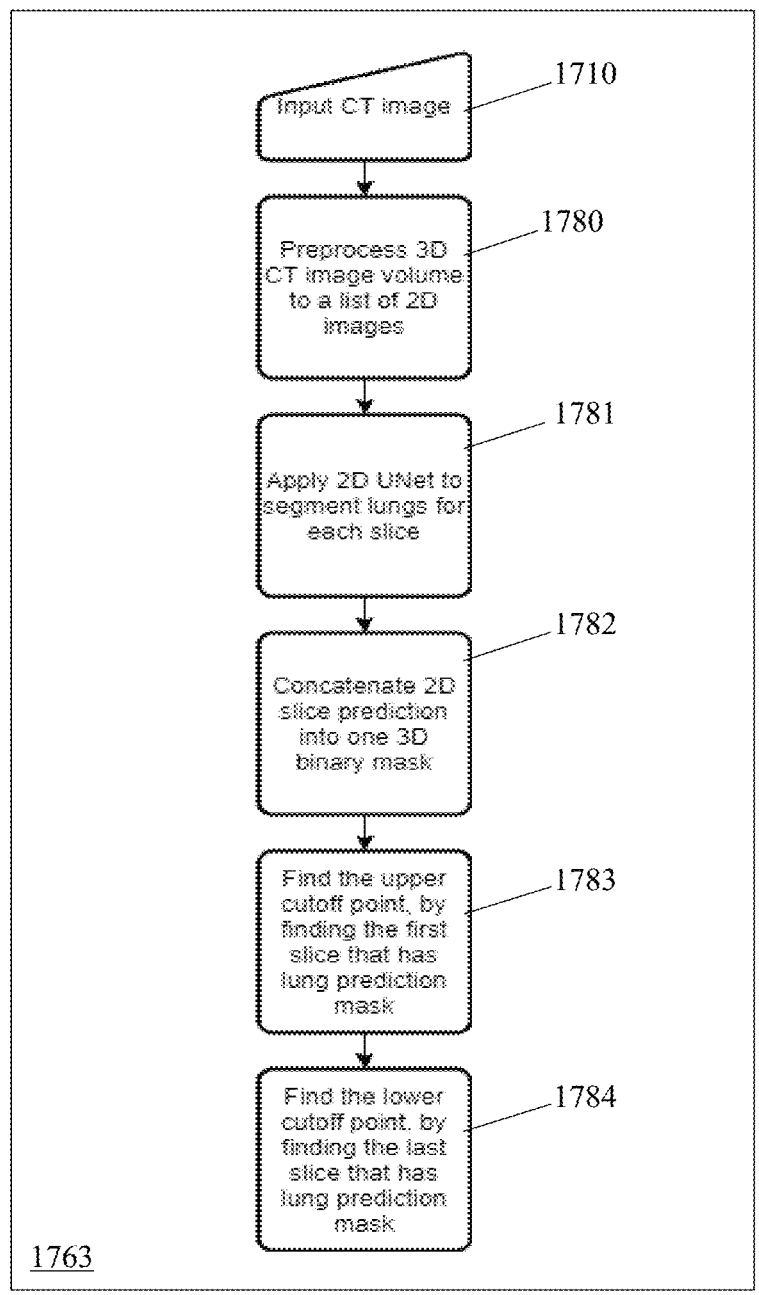
FIG. 17 is a flowchart illustrating the segmentation algorithm, element 1663, shown in FIG. 16, according to an aspect.

FIG. 17 is a flowchart illustrating the segmentation algorithm, element 1663, shown in FIG. 16, according to an aspect. As discussed previously above, the segmentation algorithm 1763 may take an input CT image and may attempt to segment at least one lung (people may possess only one lung) in the image. As shown in FIG. 17, the CT image 1710 may be inputted to the segmentation algorithm and the image 1710 may be preprocessed. At this step (1780), the volume of the 3D CT image 1710 may be converted to a 2D sequence of slices (i.e., pixels) taken from the top of the image down to the bottom of the image, as an example. Each slice of the sequence of 2D slices may then be processed through a trained convolutional neural network (CNN) well-known in the art (e.g., U-Net) to segment a lung from each slice, as shown at 1781. The trained CNN may output a 2D binary mask for each 2D slice of the original CT image 1710, wherein each 2D binary mask contains a prediction (0 or 1) of the slice containing a portion of the lung. As shown at 1782, each 2D binary mask may then be concatenated (i.e., stacked) into a final 3D binary mask ("3D binary mask," "3D segmentation mask") of the same size and shape as the original CT image 1710. The 3D segmentation mask contains the region of interest (ROI), the segmentation of the lung, wherein each 2D binary mask indicates whether or not the lung was segmented. Then, as shown at 1783, an upper cutoff point in the 3D segmentation mask may be located by finding the first slice in the 3D mask containing a lung prediction mask (i.e., successful lung segmentation), corresponding to the top-most portion of the lung. Finally, as shown at 1784, a lower cutoff point in the 3D segmentation mask may be located by finding the last slice containing a lung prediction mask, corresponding to the bottom-most portion of the lung. The upper and lower cutoff points will only be located if the 3D segmentation mask includes the segmented lungs.

As described previously when referring to FIG. 16, the segmentation algorithm 1763 attempts to segment lungs in the input CT image, which indicates that the CT image is of the thorax (chest) region. If the upper and lower cutoff points are located in the 3D segmentation mask, the segmentation of the lungs is deemed successful, and the 3D segmentation mask may be passed into the separation algorithm, which will be discussed in further detail when referring to FIGS. 19A-19B. If the upper and lower cutoff points are not located in the 3D segmentation mask, the segmentation of the lungs is deemed unsuccessful, and the CT image may be passed into the classification algorithm, which will be discussed below.

Figure 18:
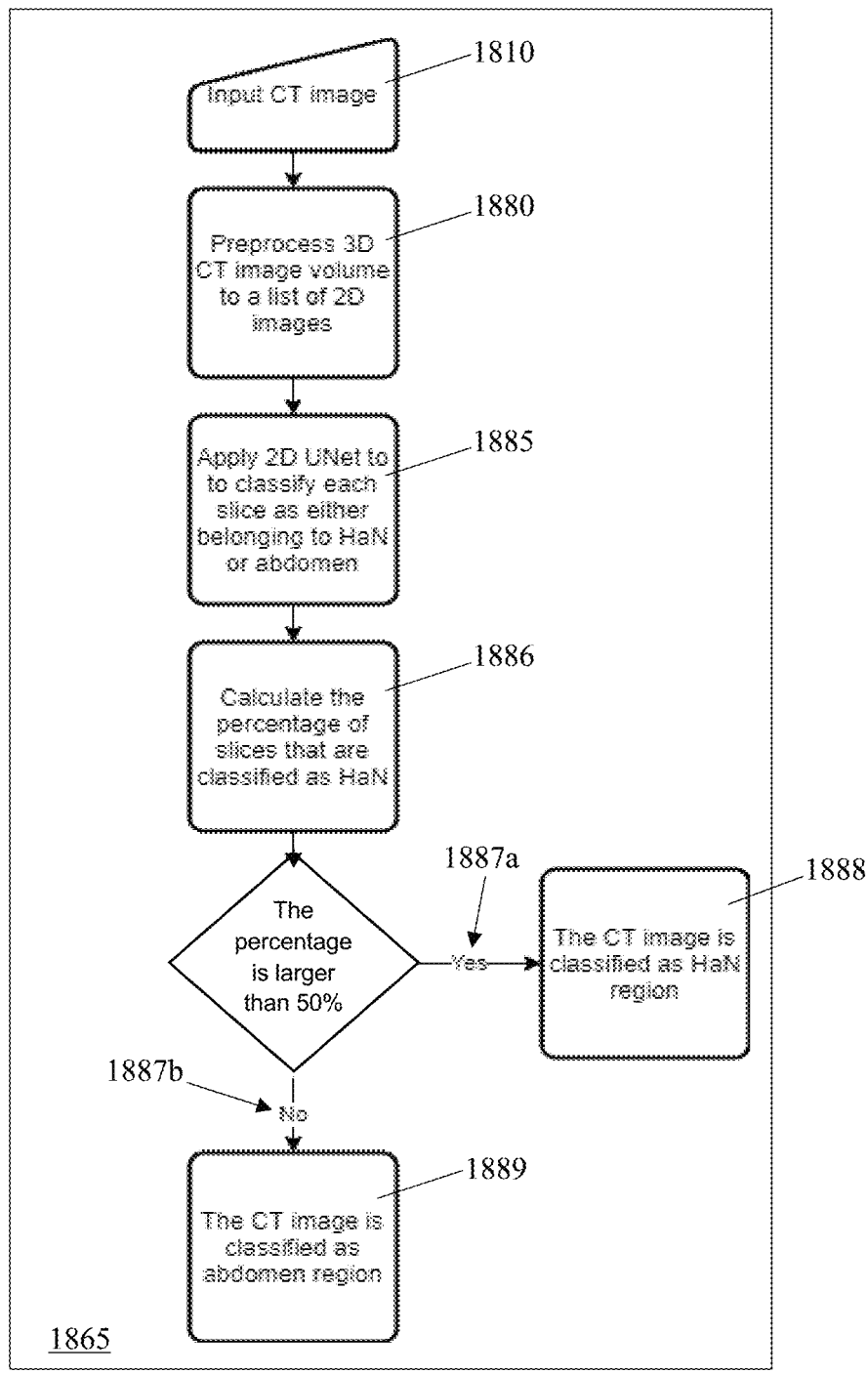
FIG. 18 is a flowchart illustrating the classification algorithm, element 1665, shown in FIG. 16, according to an aspect.

FIG. 18 is a flowchart illustrating the classification algorithm, element 1665, shown in FIG. 16, according to an aspect. As described previously when referring to FIG. 16, the classification algorithm 1865 may take an input CT image 1810 and classify the image as being either of the abdomen region or of the head and neck region. If the segmentation algorithm (1763 in FIG. 17) determines that there are no lungs in the image, the image may pass into the classification algorithm 1865 and may be preprocessed, as shown at 1880. The resulting sequence of 2D slices of the CT image 1810 may then be passed through a 2D CNN (e.g., U-Net) to classify each slice of the sequence of 2D slices, as shown at 1885. The 2D CNN functions as a binary classifier that predicts the class (either head and neck or abdomen) of each 2D slice. Then, as shown at 1886, based on the predictions of the CNN, the percentage of all the slices that were classified as being of the head and neck region may be calculated. As shown at 1887*a*, if more than half (i.e., >50%) of the slices were classified as being of the head and neck region, the CT image 1810 may be categorized as being the head and neck region (shown at 1888). Otherwise, if the percentage is less than 50% (1887*b*), the CT image 1810 may be categorized as being the abdomen region, as shown at 1889.

As discussed previously when referring to FIG. 16, once the classification algorithm 1865 classifies the CT image 1810, the image may be passed into an OAR delineation framework (1108 in FIG. 11) trained to delineate OARs of that class (e.g., in the head and neck region).

Figure 19A:
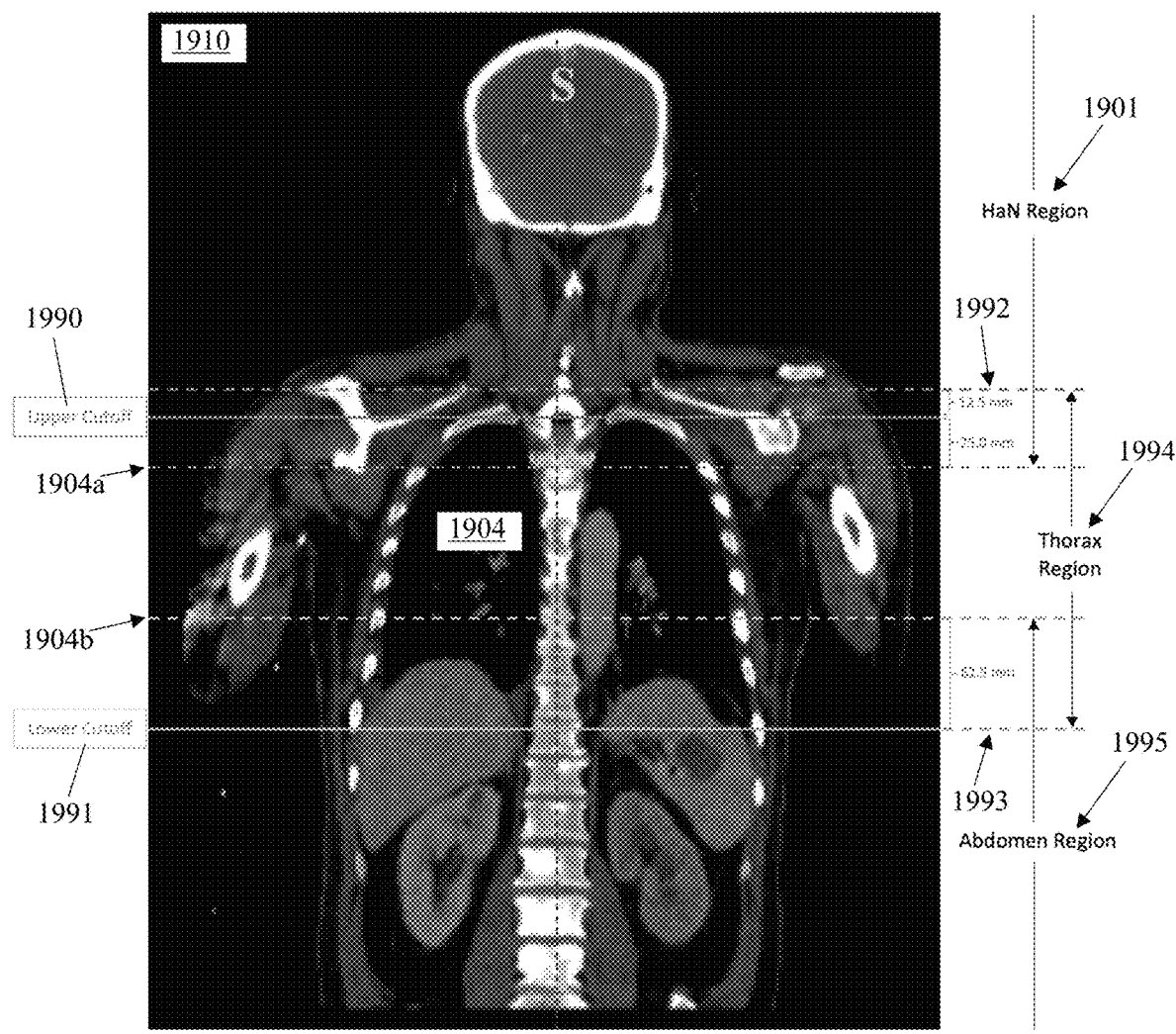
FIGS. 19A-19B illustrate exemplary images in an example of use of the method of detecting and separating regions in whole-volume medical images, according to an aspect.
Figure 19B:
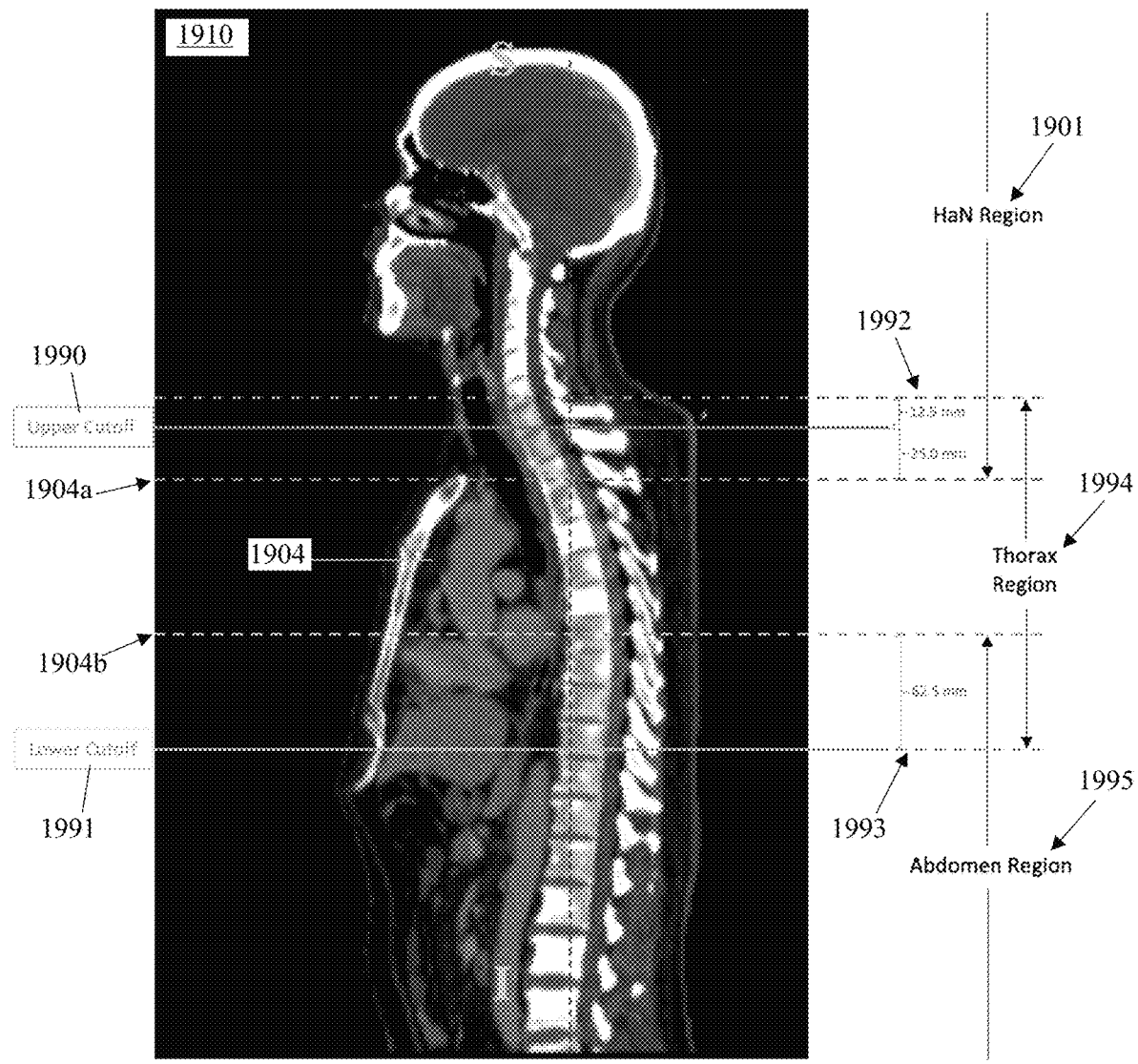

FIGS. 19A-19B illustrate exemplary images in an example of use of the method of detecting and separating regions in whole-volume medical images, according to an aspect. FIGS. 19A-19B illustrate coronal and sagittal views, respectively, of an exemplary CT image 1910. As shown in FIGS. 19A-19B, a 3D CT scan may be taken of a portion of the body containing multiple regions that may possess OARs. As such, it may be advantageous to apply the region separation method disclosed herein above to separate the regions that may be present in the CT image.

As shown in FIGS. 19A-19B, a 3D CT image 1910 may be received by the region detection model (1603) to separate the image into the distinct head and neck 1901, thorax 1994 and abdomen 1995 regions, as an example. As described above, the region detection model may separate the regions in the CT image 1910 by first attempting to segment lungs 1904 from the image 1910. As described above, the region detection model successfully segments lungs if an upper cutoff point and a lower cutoff point are located in the 3D segmentation mask. As shown, about 5 cm (50 mm) may be added above and below the top 1904*a* and bottom 1904*b* of the lungs 1904, respectively, to ensure that each OAR in the thorax region 1994 may later be delineated. The 5 cm cushion added above and below the lungs 1904 may create an upper bound 1992 and a lower bound 1993, as an example.

The separation algorithm in the region detection model may establish an upper cutoff line 1990 and a lower cutoff line 1991, from which the other regions may be defined. As shown as an example, an upper cutoff line 1990 may be drawn about 25 mm above the top 1904*a* of the lungs 1904, and a lower cutoff line 1991 may be drawn about 62.5 mm below the bottom 1904*b* of the lungs 1904. As shown in FIGS. 19A-19B, the head and neck region 1901 occupies the portion of the image 1910 above the top of the lung 1904*a*, and the abdomen region 1995 occupies the portion below the bottom of the lung 1904*b*, as an example. The separation algorithm may then cut the distinct regions in the CT image horizontally along the top and bottom of the lung, 1904*a* and 1904*b*, respectively. Thus, the region detection model disclosed herein above may accurately and efficiently detect and separate organ-containing regions of the body present in whole-volume medical images for delineation of OARs in these regions. Therefore, an advantage of the region detection method disclosed herein above may be that the user (e.g., radiation oncologist or clinician) does not need to manually separate and classify each region in a whole-volume medical image prior to OAR delineation. Another advantage of the region detection method may be that the method may still accommodate whole-volume medical images containing only a single region of the body, allowing for full implementation of the method in clinical settings.

It should be understood that there may be overlap between each region separated in a whole-volume medical image. As shown in FIGS. 19A-19B, portions of the thorax region also occupy portions of the head and neck and abdomen regions, and vice versa. As stated previously, the thorax region is slightly extended (by about 10 cm total) to ensure that each OAR in the thorax region of the body may be properly delineated. Furthermore, the head and neck region may overlap with the thorax region for scoring purposes when training the classification algorithm (1865), as an example.

It should be understood that while the region detection method disclosed above was implemented and adapted to first segment lungs in an attempt to identify the thorax region, the region detection method may be adapted to first segment other organs belonging to the thorax region before separating the other regions of the body. As an example, the region detection model could first attempt to segment the heart, which is also a part of the thorax (chest) region.

It should be understood that the two-stage deep learning OAR delineation framework and methods disclosed herein above may be adapted to process and delineate OARs present in any 3D medical image. Any whole-volume medical image such as an MRI image may be passed into the deep learning OAR delineation framework, wherein the delineation framework may output a contour map of all delineated OARs on the MRI image, as an example. It should be noted that the dataset need only be updated with manually delineated OARs in MRI images, and this new dataset passed through the system for training purposes, for the OAR delineation framework to accurately and efficiently delineate OARs in MRI images when implemented on commodity GPUs.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" or "sequence" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

As used in this application, it may be advantageous to set forth definitions of certain technical terms known to those of ordinary skills in the art. The term "voxel" means an array of elements of volume that constitute a notional three-dimensional space. The term "binary mask" means a point or volume given a value of 0 or 1. The term "batch" means a hyperparameter that controls the number of training samples to work through before the model's internal parameters are updated. The term "patch" means a subsection of an input image to the model. The term "kernel" means filter or feature detector. The term "tensor" means a multidimensional array or matrix.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/ or examples. Hence, the scope of the invention is defined by the accompanying claims and their equivalents. Further, each and every claim is incorporated as further disclosure into the specification.

What is claimed is:

1. A method of automatically delineating at least one organs-at-risk (OAR) present in a whole-volume medical image, the method comprising the steps of:
    inputting the whole-volume medical image into a two-stage deep convolutional neural network (DCNN) model, the whole-volume medical image being defined by a first feature map of a first size, and the two-stage DCNN model comprising:
        an OAR detection network operating during a first stage of the two-stage DCNN model; and
        an OAR segmentation network operating during a second stage of the two-stage DCNN model;
    extracting image features from the first feature map through a sequence of downsampling blocks, followed by an upsampling block, such that a final detection feature map of a final size is generated;
    detecting at least one OAR candidate by branching the final detection feature map into a bounding box regressions block and a binary classification block;
    generating a predicted bounding box defined by the bounding box regressions block, the predicted bounding box identifying an approximate size and location of the at least one OAR candidate, and assigning a corresponding class label classifying the at least one OAR candidate;
    once passed into the OAR segmentation network, cropping the final detection feature map, and a feature map of at least one downsampling block from the OAR detection network, according to the approximate size and location identified by the predicted bounding box;
    generating a final segmentation feature map through a sequence of upsampling blocks and subsequent concatenation of the cropped final detection feature map with the cropped feature map of the at least one downsampling block; and
    generating at least one predicted binary mask delineating the at least one OAR in the whole-volume medical image, wherein the at least one predicted binary mask is a size equal to the first size of the first feature map.

2. The method of claim 1 further comprising outputting a contour map outlined by the at least one predicted binary mask transposed over the whole-volume medical image, the contour map illustrating the at least one delineated OAR.

3. The method of claim 1, wherein the first size of the first feature map is the product of D×H×W, wherein D denotes depth, H denotes height and W denotes width.

4. The method of claim 1, wherein the final size of the final detection feature map is the product of D/8×H/8×W/8, wherein D denotes depth, H denotes height and W denotes width.

5. The method of claim 1, wherein the extracting image features from the first feature map is performed by:
  when passing through the sequence of downsampling blocks, applying 3D convolution to the first feature map; and
  when passing through the upsampling block, applying transposed convolution and subsequent concatenation with a feature map of a same size in a corresponding downsampling block.

6. The method of claim 1, wherein the branching the final detection feature map is performed by applying a 3×3×3 convolution followed by a 1×1×1 convolution.

7. The method of claim 1, wherein the generating a predicted bounding box is performed by:
  applying a Region of Interest (ROI)-pooling in regions of the final detection feature map specified by the predicted bounding box; and
  subsequently applying two fully connected layers to classify the at least one OAR candidate.

8. The method of claim 1, wherein each upsampling block of the sequence of upsampling blocks comprises a trilinear upsampling layer, followed by a 3D convolution sub-block and local contrast normalization.

9. The method of claim 8, wherein the local contrast normalization is defined by:

$$\gamma_{cijk} = \frac{x_{cijk} - \mu_c}{\sqrt{\sigma_c^2 + \epsilon}}.$$

10. The method of claim 1, wherein the generating at least one predicted binary mask is performed by:
  applying a 1×1×1 convolution to the final segmentation feature map, chosen according to the class label; and
  subsequently applying a sigmoid transformation.

11. An organs-at-risk (OAR) automatic contouring computer system for conducting delineation of OARs in whole-volume medical images, the computer system comprising:
  a deep convolutional neural network (DCNN) trained to delineate at least one OAR, the DCNN comprising:
    an OAR detection network adapted to receive at least one whole-volume medical input image and output at least one detected OAR candidate, the OAR detection network comprising:
      a sequence of downsampling blocks adapted to receive the at least one whole-volume medical input image;
      an upsampling block in communication with the sequence of downsampling blocks;
      a detection loss function adapted to receive a final detection feature map from the upsampling block; and
      a classification loss function adapted to receive at least one predicted bounding box of the final detection feature map; and
    an OAR segmentation network adapted to receive the at least one detected OAR candidate from the OAR detection network and output a contour map transposed over the at least one whole-volume medical input image, the contour map delineating the at least one OAR, and the OAR segmentation network comprising:
      a sequence of upsampling blocks and subsequent concatenation adapted to receive the at least one detected OAR candidate; and
      a segmentation loss function adapted to receive a final segmentation feature map from the sequence of upsampling blocks and subsequent concatenation;
  wherein the DCNN is adapted to be trained by passing a training set comprising manually delineated OARs in whole-volume medical images through the detection, classification and segmentation loss functions in the DCNN.

12. The system of claim 11, wherein each downsampling block of the sequence of downsampling blocks comprises at least one 3D convolution residual sub-block.

13. The system of claim 11, wherein each upsampling block of the sequence of upsampling blocks comprises a trilinear upsampling layer, followed by a 3D convolution sub-block and local contrast normalization.

14. The system of claim 13, wherein the local contrast normalization is defined by:

$$\gamma_{cijk} = \frac{x_{cijk} - \mu_c}{\sqrt{\sigma_c^2 + \epsilon}}.$$

15. The system of claim 11, wherein the detection loss function is defined by:

$$\mathcal{L}_d(\{P_i\}, \{t_i\}) = \frac{1}{N_{cls}} \sum_i \mathcal{L}_{cls}(P_i, P_i^*) + \lambda \frac{1}{N_{reg}} \sum_i \mathcal{L}_{reg}(t_i, t_i^*).$$

16. The system of claim 11, wherein the segmentation loss function is defined by:
$$\mathcal{L}_s = \Sigma_{c=1}^{28} I(c)(1-\phi(m^c, g^c)).$$

* * * * *